US008277488B2

(12) United States Patent
Altarac et al.

(10) Patent No.: US 8,277,488 B2
(45) Date of Patent: Oct. 2, 2012

(54) INTERSPINOUS SPACER

(75) Inventors: Moti Altarac, Irvine, CA (US); Shawn Tebbe, Oceanside, CA (US); Joey Camia Reglos, Lake Forest, CA (US); Yang Cheng, Foothill Ranch, CA (US); Murali P. Kadaba, Foster City, CA (US); Daniel H. Kim, Houston, TX (US)

(73) Assignee: VertiFlex, Inc., San Clemente, CA (US)

( * ) Notice: Subject to any disclaimer, the term of this patent is extended or adjusted under 35 U.S.C. 154(b) by 574 days.

(21) Appl. No.: 12/220,427

(22) Filed: Jul. 24, 2008

(65) Prior Publication Data
US 2008/0294263 A1 Nov. 27, 2008

Related U.S. Application Data

(63) Continuation-in-part of application No. 12/217,662, filed on Jul. 8, 2008, which is a continuation-in-part of application No. 12/148,104, filed on Apr. 16, 2008, which is a continuation-in-part of application No. 11/593,995, filed on Nov. 7, 2006, which is a continuation-in-part of application No. 11/582,874, filed on Oct. 18, 2006, now Pat. No. 8,128,662, which is a continuation-in-part of application No. 11/314,712, filed on Dec. 20, 2005, now Pat. No. 8,152,837, which is a continuation-in-part of application No. 11/190,496, filed on Jul. 26, 2005, which is a continuation-in-part of application No. 11/079,006, filed on Mar. 10, 2005, now Pat. No. 8,012,207, which is a continuation-in-part of application No. 11/052,002, filed on Feb. 4, 2005, which is a continuation-in-part of application No. 11/006,502, filed on Dec. 6, 2004, now Pat. No. 8,123,807, which is a continuation-in-part of application No. 10/970,843, filed on Oct. 20, 2004, now Pat. No. 8,167,944.

(60) Provisional application No. 60/961,741, filed on Jul. 24, 2007, provisional application No. 60/958,876, filed on Jul. 9, 2007, provisional application No. 60/923,971, filed on Apr. 17, 2007, provisional application No. 60/923,841, filed on Apr. 16, 2007.

(51) Int. Cl.
*A61F 2/44* (2006.01)
(52) U.S. Cl. .................................. 606/249; 623/17.11
(58) Field of Classification Search .................. 606/249, 606/248; 623/17.11, 17.15, 17.16
See application file for complete search history.

(56) References Cited

U.S. PATENT DOCUMENTS
2,248,054 A 7/1941 Becker
(Continued)

FOREIGN PATENT DOCUMENTS
DE 69507480 T2 9/1999
(Continued)

OTHER PUBLICATIONS
Final Office Action; U.S. Appl. No. 11/006,502; Mailing Date: Aug. 17, 2009, 7 pages.
(Continued)

*Primary Examiner* — Christopher D Koharski
*Assistant Examiner* — Christopher D Prone
(74) *Attorney, Agent, or Firm* — Perkins Coie LLP

(57) ABSTRACT

An implantable spacer for placement between adjacent spinous processes in a spinal motion segment is provided. The spacer includes a body defining a longitudinal axis and passageway. A first arm and a second arm are connected to the body. Each arm has a pair of extensions and a saddle defining a U-shaped configuration for seating a spinous process therein. Each arm has a proximal caming surface and is capable of rotation with respect to the body. An actuator assembly is disposed inside the passageway and connected to the body. When advanced, a threaded shaft of the actuator assembly contacts the caming surfaces of arms to rotate them from an undeployed configuration to a deployed configuration. In the deployed configuration, the distracted adjacent spinous processes are seated in the U-shaped portion of the arms.

36 Claims, 25 Drawing Sheets

U.S. PATENT DOCUMENTS

| | | |
|---|---|---|
| 2,677,369 A | 5/1954 | Knowles |
| 3,242,120 A | 3/1966 | Steuber |
| 3,648,691 A | 3/1972 | Lumb et al. |
| 3,986,383 A | 10/1976 | Petteys |
| 4,632,101 A | 12/1986 | Freedland |
| 4,685,447 A | 8/1987 | Iversen et al. |
| 4,895,564 A | 1/1990 | Farrell |
| 5,011,484 A | 4/1991 | Breard |
| 5,015,247 A | 5/1991 | Michelson |
| 5,019,081 A | 5/1991 | Watanabe |
| 5,059,193 A | 10/1991 | Kuslich |
| 5,092,866 A | 3/1992 | Breard et al. |
| 5,180,393 A | 1/1993 | Commarmond |
| 5,182,281 A | 1/1993 | Frigola-Constansa et al. |
| 5,188,281 A | 2/1993 | Fujiwara et al. |
| 5,192,281 A | 3/1993 | de la Caffiniere |
| 5,195,526 A | 3/1993 | Michelson |
| 5,298,253 A | 3/1994 | LeFiles et al. |
| 5,368,594 A | 11/1994 | Martin et al. |
| 5,390,683 A | 2/1995 | Pisharodi |
| 5,415,661 A | 5/1995 | Holmes |
| 5,456,722 A | 10/1995 | McLeod et al. |
| 5,462,738 A | 10/1995 | LeFiles et al. |
| 5,472,452 A | 12/1995 | Trott |
| 5,484,437 A | 1/1996 | Michelson |
| 5,487,739 A | 1/1996 | Aebischer et al. |
| 5,489,308 A | 2/1996 | Kuslich et al. |
| 5,496,318 A | 3/1996 | Howland et al. |
| 5,531,748 A | 7/1996 | De La Caffiniere |
| 5,549,679 A | 8/1996 | Kuslich |
| 5,571,189 A | 11/1996 | Kuslich |
| 5,591,165 A | 1/1997 | Jackson |
| 5,609,634 A | 3/1997 | Voydeville |
| 5,609,636 A | 3/1997 | Kohrs et al. |
| 5,645,599 A | 7/1997 | Samani |
| 5,654,599 A | 8/1997 | Casper |
| 5,658,337 A | 8/1997 | Kohrs et al. |
| 5,674,295 A | 10/1997 | Ray et al. |
| 5,700,264 A | 12/1997 | Zucherman et al. |
| 5,725,582 A | 3/1998 | Bevan et al. |
| 5,741,253 A | 4/1998 | Michelson |
| 5,762,629 A | 6/1998 | Kambin |
| 5,836,948 A | 11/1998 | Zucherman et al. |
| 5,860,977 A | 1/1999 | Zucherman et al. |
| 5,863,948 A | 1/1999 | Epstein et al. |
| 5,876,404 A | 3/1999 | Zucherman et al. |
| RE36,211 E | 5/1999 | Nonomura |
| 5,904,636 A | 5/1999 | Chen et al. |
| 5,904,686 A | 5/1999 | Zucherman et al. |
| 5,972,015 A | 10/1999 | Scribner et al. |
| 6,039,761 A | 3/2000 | Li et al. |
| 6,045,552 A | 4/2000 | Zucherman et al. |
| 6,048,342 A | 4/2000 | Zucherman et al. |
| 6,066,154 A | 5/2000 | Reiley et al. |
| 6,068,630 A | 5/2000 | Zucherman et al. |
| 6,074,390 A | 6/2000 | Zucherman et al. |
| 6,080,155 A | 6/2000 | Michelson |
| 6,080,157 A | 6/2000 | Cathro et al. |
| 6,090,112 A | 7/2000 | Zucherman et al. |
| 6,096,038 A | 8/2000 | Michelson |
| 6,102,928 A | 8/2000 | Bonutti |
| D433,193 S | 10/2000 | Gaw et al. |
| 6,132,464 A | 10/2000 | Martin et al. |
| 6,149,642 A | 11/2000 | Gerhart et al. |
| 6,149,652 A | 11/2000 | Zucherman et al. |
| 6,152,926 A | 11/2000 | Zucherman et al. |
| 6,156,038 A | 12/2000 | Zucherman et al. |
| 6,159,215 A | 12/2000 | Urbahns et al. |
| 6,179,873 B1 | 1/2001 | Zientek |
| 6,183,471 B1 | 2/2001 | Zucherman et al. |
| 6,190,387 B1 | 2/2001 | Zucherman et al. |
| 6,225,048 B1 | 5/2001 | Soderberg-Naucler et al. |
| 6,235,030 B1 | 5/2001 | Zucherman et al. |
| 6,238,397 B1 | 5/2001 | Zucherman et al. |
| 6,264,651 B1 | 7/2001 | Underwood et al. |
| 6,264,656 B1 | 7/2001 | Michelson |
| 6,267,765 B1 | 7/2001 | Taylor et al. |
| 6,270,498 B1 | 8/2001 | Michelson |
| 6,280,444 B1 | 8/2001 | Zucherman et al. |
| 6,312,431 B1 | 11/2001 | Asfora |
| 6,332,882 B1 | 12/2001 | Zucherman et al. |
| 6,332,883 B1 | 12/2001 | Zucherman et al. |
| 6,336,930 B1 | 1/2002 | Stalcup et al. |
| 6,348,053 B1 | 2/2002 | Cachia |
| 6,364,883 B1 | 4/2002 | Santilli |
| 6,371,989 B1 | 4/2002 | Chauvin et al. |
| 6,375,682 B1 | 4/2002 | Fleischmann et al. |
| 6,379,355 B1 | 4/2002 | Zucherman et al. |
| 6,395,032 B1 | 5/2002 | Gauchet et al. |
| 6,402,740 B1 | 6/2002 | Ellis et al. |
| 6,402,750 B1 | 6/2002 | Atkinson et al. |
| 6,402,784 B1 | 6/2002 | Wardlaw et al. |
| 6,413,228 B1 | 7/2002 | Hung et al. |
| 6,419,676 B1 | 7/2002 | Zucherman et al. |
| 6,419,677 B2 | 7/2002 | Zucherman et al. |
| 6,440,169 B1 | 8/2002 | Elberg et al. |
| 6,443,988 B2 | 9/2002 | Felt et al. |
| 6,447,547 B1 | 9/2002 | Michelson |
| 6,451,019 B1 | 9/2002 | Zucherman et al. |
| 6,451,020 B1 | 9/2002 | Zucherman et al. |
| 6,471,976 B1 | 10/2002 | Taylor et al. |
| 6,478,796 B2 | 11/2002 | Zucherman et al. |
| 6,478,822 B1 | 11/2002 | Leroux et al. |
| 6,500,178 B2 | 12/2002 | Zucherman et al. |
| 6,514,256 B2 | 2/2003 | Zucherman et al. |
| 6,530,925 B2 | 3/2003 | Boudard et al. |
| 6,558,333 B2 | 5/2003 | Gilboa et al. |
| 6,565,570 B2 | 5/2003 | Sterett et al. |
| 6,572,617 B1 | 6/2003 | Senegas |
| 6,575,981 B1 | 6/2003 | Boyd et al. |
| 6,579,319 B2 | 6/2003 | Goble et al. |
| 6,582,433 B2 | 6/2003 | Yun |
| 6,582,451 B1 | 6/2003 | Marucci et al. |
| 6,610,065 B1 | 8/2003 | Branch et al. |
| 6,610,091 B1 | 8/2003 | Reiley |
| 6,626,944 B1 | 9/2003 | Taylor |
| 6,645,207 B2 | 11/2003 | Dixon et al. |
| 6,645,211 B2 | 11/2003 | Magana |
| 6,652,527 B2 | 11/2003 | Zucherman et al. |
| 6,652,534 B2 | 11/2003 | Zucherman et al. |
| 6,679,886 B2 | 1/2004 | Weikel et al. |
| 6,695,842 B2 | 2/2004 | Zucherman et al. |
| 6,699,246 B2 | 3/2004 | Zucherman et al. |
| 6,699,247 B2 | 3/2004 | Zucherman et al. |
| 6,712,819 B2 | 3/2004 | Zucherman et al. |
| 6,716,245 B2 | 4/2004 | Pasquet et al. |
| 6,733,534 B2 | 5/2004 | Sherman |
| 6,746,485 B1 | 6/2004 | Zucherman et al. |
| 6,761,720 B1 | 7/2004 | Senegas |
| 6,769,983 B2 | 8/2004 | Slomiany |
| 6,783,529 B2 | 8/2004 | Hover et al. |
| 6,796,983 B1 | 9/2004 | Zucherman et al. |
| 6,835,205 B2 | 12/2004 | Atkinson et al. |
| 6,858,029 B2 | 2/2005 | Yeh et al. |
| 6,869,398 B2 | 3/2005 | Obenchain et al. |
| 6,902,566 B2 | 6/2005 | Zucherman et al. |
| 6,926,728 B2 | 8/2005 | Zucherman et al. |
| 6,946,000 B2 | 9/2005 | Senegas et al. |
| 6,949,123 B2 | 9/2005 | Reiley |
| 6,966,930 B2 | 11/2005 | Arnin et al. |
| 6,974,478 B2 | 12/2005 | Reiley et al. |
| 7,011,685 B2 | 3/2006 | Arnin et al. |
| 7,029,473 B2 | 4/2006 | Zucherman et al. |
| 7,033,358 B2 | 4/2006 | Taylor et al. |
| 7,048,736 B2 | 5/2006 | Robinson et al. |
| 7,070,598 B2 | 7/2006 | Lim et al. |
| 7,083,649 B2 | 8/2006 | Zucherman et al. |
| 7,087,055 B2 | 8/2006 | Lim et al. |
| 7,087,083 B2 | 8/2006 | Pasquet et al. |
| 7,097,648 B1 | 8/2006 | Globerman et al. |
| 7,101,375 B2 | 9/2006 | Zucherman et al. |
| 7,163,558 B2 | 1/2007 | Senegas et al. |
| 7,179,225 B2 | 2/2007 | Shluzas et al. |
| 7,187,064 B2 | 3/2007 | Tzu et al. |
| 7,189,236 B2 | 3/2007 | Taylor et al. |
| 7,201,751 B2 | 4/2007 | Zucherman et al. |
| 7,217,291 B2 | 5/2007 | Zucherman et al. |

| Patent No. | Date | Inventor |
|---|---|---|
| 7,223,289 B2 | 5/2007 | Trieu et al. |
| 7,229,441 B2 | 6/2007 | Trieu et al. |
| 7,252,673 B2 | 8/2007 | Lim |
| 7,282,063 B2 | 10/2007 | Cohen et al. |
| 7,318,839 B2 | 1/2008 | Malberg et al. |
| 7,320,707 B2 | 1/2008 | Zucherman et al. |
| 7,335,200 B2 | 2/2008 | Carli |
| 7,335,203 B2 | 2/2008 | Winslow et al. |
| 7,354,453 B2 | 4/2008 | McAfee |
| 7,384,340 B2 | 6/2008 | Eguchi et al. |
| 7,410,501 B2 | 8/2008 | Michelson |
| 7,481,840 B2 | 1/2009 | Zucherman et al. |
| 7,491,204 B2 | 2/2009 | Marnay et al. |
| 7,497,859 B2 | 3/2009 | Zucherman et al. |
| 7,503,935 B2 | 3/2009 | Zucherman et al. |
| 7,504,798 B2 | 3/2009 | Kawada et al. |
| 7,520,899 B2 | 4/2009 | Zucherman et al. |
| 7,547,308 B2 | 6/2009 | Bertagnoli et al. |
| 7,550,009 B2 | 6/2009 | Arnin et al. |
| 7,565,259 B2 | 7/2009 | Sheng et al. |
| 7,572,276 B2 | 8/2009 | Lim et al. |
| 7,575,600 B2 | 8/2009 | Zucherman et al. |
| 7,591,851 B2 | 9/2009 | Winslow et al. |
| 7,601,170 B2 | 10/2009 | Winslow et al. |
| 7,635,378 B2 | 12/2009 | Zucherman et al. |
| 7,637,950 B2 | 12/2009 | Baccelli et al. |
| 7,662,187 B2 | 2/2010 | Zucherman et al. |
| 7,670,377 B2 | 3/2010 | Zucherman et al. |
| 7,682,376 B2 | 3/2010 | Trieu |
| 7,691,146 B2 | 4/2010 | Zucherman et al. |
| 7,699,852 B2 | 4/2010 | Frankel et al. |
| 7,742,795 B2 | 6/2010 | Stone et al. |
| 7,758,619 B2 | 7/2010 | Zucherman et al. |
| 7,763,050 B2 | 7/2010 | Winslow et al. |
| 7,776,090 B2 | 8/2010 | Winslow et al. |
| 7,837,734 B2 | 11/2010 | Zucherman et al. |
| 7,846,183 B2 | 12/2010 | Blain |
| 7,857,815 B2 | 12/2010 | Zucherman et al. |
| 7,862,569 B2 | 1/2011 | Zucherman et al. |
| 7,862,586 B2 | 1/2011 | Malek |
| 2001/0031965 A1 | 10/2001 | Zucherman et al. |
| 2002/0029083 A1 | 3/2002 | Zucherman et al. |
| 2002/0072752 A1 | 6/2002 | Zucherman et al. |
| 2002/0143331 A1 | 10/2002 | Zucherman et al. |
| 2003/0040746 A1 | 2/2003 | Mitchell et al. |
| 2003/0074075 A1 | 4/2003 | Thomas et al. |
| 2003/0149438 A1 | 8/2003 | Nichols et al. |
| 2003/0153976 A1 | 8/2003 | Cauthen et al. |
| 2003/0176921 A1 | 9/2003 | Lawson |
| 2003/0220643 A1 | 11/2003 | Ferree |
| 2003/0220650 A1 | 11/2003 | Major et al. |
| 2004/0006341 A1 | 1/2004 | Shaolian et al. |
| 2004/0087947 A1 | 5/2004 | Lim et al. |
| 2004/0106995 A1 | 6/2004 | Le Couedic et al. |
| 2004/0153065 A1 | 8/2004 | Lim |
| 2004/0162617 A1 | 8/2004 | Zucherman et al. |
| 2004/0167625 A1 | 8/2004 | Beyar et al. |
| 2004/0172135 A1 | 9/2004 | Mitchell |
| 2004/0181282 A1 | 9/2004 | Zucherman et al. |
| 2004/0193159 A1 | 9/2004 | Zucherman et al. |
| 2004/0199255 A1 | 10/2004 | Mathieu et al. |
| 2004/0220568 A1 | 11/2004 | Zucherman et al. |
| 2004/0243239 A1 | 12/2004 | Taylor |
| 2005/0010293 A1 | 1/2005 | Zucherman et al. |
| 2005/0010298 A1 | 1/2005 | Zucherman et al. |
| 2005/0033295 A1 | 2/2005 | Wisnewski |
| 2005/0049708 A1 | 3/2005 | Atkinson et al. |
| 2005/0075634 A1 | 4/2005 | Zucherman et al. |
| 2005/0085813 A1 | 4/2005 | Spitler et al. |
| 2005/0101955 A1 | 5/2005 | Zucherman et al. |
| 2005/0125063 A1 | 6/2005 | Matge et al. |
| 2005/0125066 A1 | 6/2005 | McAfee |
| 2005/0143738 A1 | 6/2005 | Zucherman et al. |
| 2005/0165398 A1 | 7/2005 | Reiley |
| 2005/0182416 A1 | 8/2005 | Lim et al. |
| 2005/0192586 A1 | 9/2005 | Zucherman et al. |
| 2005/0192671 A1 | 9/2005 | Bao et al. |
| 2005/0196420 A1 | 9/2005 | Zucherman et al. |
| 2005/0203512 A1 | 9/2005 | Hawkins et al. |
| 2005/0209603 A1 | 9/2005 | Zucherman et al. |
| 2005/0216087 A1 | 9/2005 | Zucherman et al. |
| 2005/0228383 A1 | 10/2005 | Zucherman et al. |
| 2005/0228384 A1 | 10/2005 | Zucherman et al. |
| 2005/0228426 A1 | 10/2005 | Campbell |
| 2005/0240182 A1 | 10/2005 | Zucherman et al. |
| 2005/0245937 A1 | 11/2005 | Winslow |
| 2005/0261768 A1 | 11/2005 | Trieu |
| 2005/0278028 A1 | 12/2005 | Mujwid |
| 2006/0036258 A1 | 2/2006 | Zucherman et al. |
| 2006/0064165 A1 | 3/2006 | Zucherman et al. |
| 2006/0064166 A1 | 3/2006 | Zucherman et al. |
| 2006/0074431 A1 | 4/2006 | Sutton et al. |
| 2006/0084976 A1 | 4/2006 | Borgstrom et al. |
| 2006/0084983 A1 | 4/2006 | Kim |
| 2006/0084985 A1 | 4/2006 | Kim |
| 2006/0084988 A1 | 4/2006 | Kim |
| 2006/0084991 A1 | 4/2006 | Borgstrom et al. |
| 2006/0085069 A1 | 4/2006 | Kim |
| 2006/0085070 A1 | 4/2006 | Kim |
| 2006/0085074 A1 | 4/2006 | Raiszadeh |
| 2006/0089718 A1 | 4/2006 | Zucherman et al. |
| 2006/0102269 A1 | 5/2006 | Uchida et al. |
| 2006/0122620 A1 | 6/2006 | Kim |
| 2006/0149254 A1 | 7/2006 | Lauryssen et al. |
| 2006/0149289 A1 | 7/2006 | Winslow et al. |
| 2006/0167416 A1 | 7/2006 | Mathis et al. |
| 2006/0190083 A1 | 8/2006 | Arnin et al. |
| 2006/0195102 A1 | 8/2006 | Malandain |
| 2006/0217726 A1 | 9/2006 | Maxy et al. |
| 2006/0217811 A1 | 9/2006 | Lambrecht et al. |
| 2006/0224159 A1 | 10/2006 | Anderson |
| 2006/0235386 A1 | 10/2006 | Anderson |
| 2006/0235387 A1 | 10/2006 | Peterman |
| 2006/0235521 A1 | 10/2006 | Zucherman et al. |
| 2006/0241597 A1 | 10/2006 | Mitchell et al. |
| 2006/0241610 A1 | 10/2006 | Lim et al. |
| 2006/0241613 A1 | 10/2006 | Bruneau et al. |
| 2006/0241614 A1 | 10/2006 | Bruneau et al. |
| 2006/0241757 A1 | 10/2006 | Anderson |
| 2006/0247623 A1 | 11/2006 | Anderson et al. |
| 2006/0247632 A1 | 11/2006 | Winslow et al. |
| 2006/0247633 A1 | 11/2006 | Winslow et al. |
| 2006/0247640 A1 | 11/2006 | Blackwell et al. |
| 2006/0247650 A1 | 11/2006 | Yerby et al. |
| 2006/0247773 A1 | 11/2006 | Stamp |
| 2006/0264938 A1 | 11/2006 | Zucherman et al. |
| 2006/0264939 A1 | 11/2006 | Zucherman et al. |
| 2006/0265066 A1 | 11/2006 | Zucherman et al. |
| 2006/0265067 A1 | 11/2006 | Zucherman et al. |
| 2006/0271049 A1 | 11/2006 | Zucherman et al. |
| 2006/0271055 A1 | 11/2006 | Thramann |
| 2006/0271061 A1 | 11/2006 | Beyar et al. |
| 2006/0271194 A1* | 11/2006 | Zucherman et al. ........ 623/17.11 |
| 2006/0276801 A1 | 12/2006 | Yerby et al. |
| 2006/0276897 A1 | 12/2006 | Winslow et al. |
| 2006/0282075 A1 | 12/2006 | Labrom et al. |
| 2006/0282077 A1 | 12/2006 | Labrom et al. |
| 2006/0282078 A1 | 12/2006 | Labrom et al. |
| 2006/0282079 A1 | 12/2006 | Labrom et al. |
| 2006/0293662 A1 | 12/2006 | Boyer, II et al. |
| 2007/0010813 A1 | 1/2007 | Zucherman et al. |
| 2007/0016196 A1 | 1/2007 | Winslow et al. |
| 2007/0032790 A1* | 2/2007 | Aschmann et al. ............. 606/61 |
| 2007/0055237 A1 | 3/2007 | Edidin et al. |
| 2007/0055246 A1 | 3/2007 | Zucherman et al. |
| 2007/0073289 A1 | 3/2007 | Kwak et al. |
| 2007/0093830 A1 | 4/2007 | Zucherman et al. |
| 2007/0100340 A1 | 5/2007 | Lange et al. |
| 2007/0100366 A1 | 5/2007 | Dziedzic et al. |
| 2007/0106298 A1 | 5/2007 | Carli et al. |
| 2007/0106385 A1 | 5/2007 | Zucherman et al. |
| 2007/0118120 A1 | 5/2007 | Farris et al. |
| 2007/0123863 A1 | 5/2007 | Winslow et al. |
| 2007/0123904 A1 | 5/2007 | Stad et al. |
| 2007/0142915 A1 | 6/2007 | Altarac et al. |
| 2007/0161991 A1 | 7/2007 | Altarac et al. |
| 2007/0161992 A1 | 7/2007 | Kwak et al. |
| 2007/0161993 A1 | 7/2007 | Lowery et al. |

| | | | | | | |
|---|---|---|---|---|---|---|
| 2007/0162005 A1 | 7/2007 | Peterson et al. | | 2008/0021561 A1 | 1/2008 | Zucherman et al. |
| 2007/0173818 A1 | 7/2007 | Hestad et al. | | 2008/0027545 A1 | 1/2008 | Zucherman et al. |
| 2007/0173821 A1 | 7/2007 | Trieu | | 2008/0027552 A1 | 1/2008 | Zucherman et al. |
| 2007/0173822 A1 | 7/2007 | Bruneau et al. | | 2008/0027553 A1 | 1/2008 | Zucherman et al. |
| 2007/0173823 A1 | 7/2007 | Dewey et al. | | 2008/0033445 A1 | 2/2008 | Zucherman et al. |
| 2007/0173832 A1 | 7/2007 | Altarac et al. | | 2008/0033553 A1 | 2/2008 | Zucherman et al. |
| 2007/0173939 A1 | 7/2007 | Kim et al. | | 2008/0033558 A1 | 2/2008 | Zucherman et al. |
| 2007/0179500 A1 | 8/2007 | Chin et al. | | 2008/0033559 A1 | 2/2008 | Zucherman et al. |
| 2007/0185490 A1 | 8/2007 | Implicito | | 2008/0039853 A1 | 2/2008 | Zucherman et al. |
| 2007/0191834 A1 | 8/2007 | Bruneau et al. | | 2008/0039858 A1 | 2/2008 | Zucherman et al. |
| 2007/0191847 A1 | 8/2007 | Arnin et al. | | 2008/0039859 A1 | 2/2008 | Zucherman et al. |
| 2007/0191947 A1 | 8/2007 | Arnin et al. | | 2008/0039945 A1 | 2/2008 | Zucherman et al. |
| 2007/0191948 A1 | 8/2007 | Arnin et al. | | 2008/0039946 A1 | 2/2008 | Zucherman et al. |
| 2007/0191949 A1 | 8/2007 | Arnin et al. | | 2008/0039947 A1 | 2/2008 | Zucherman et al. |
| 2007/0191950 A1 | 8/2007 | Arnin et al. | | 2008/0045958 A1 | 2/2008 | Zucherman et al. |
| 2007/0198045 A1 | 8/2007 | Morton et al. | | 2008/0045959 A1 | 2/2008 | Zucherman et al. |
| 2007/0198091 A1 | 8/2007 | Boyer et al. | | 2008/0046081 A1 | 2/2008 | Zucherman et al. |
| 2007/0203490 A1 | 8/2007 | Zucherman et al. | | 2008/0046085 A1 | 2/2008 | Zucherman et al. |
| 2007/0203493 A1 | 8/2007 | Zucherman et al. | | 2008/0046086 A1 | 2/2008 | Zucherman et al. |
| 2007/0203494 A1 | 8/2007 | Arnin et al. | | 2008/0046087 A1 | 2/2008 | Zucherman et al. |
| 2007/0203495 A1 | 8/2007 | Zucherman et al. | | 2008/0046088 A1 | 2/2008 | Zucherman et al. |
| 2007/0203496 A1 | 8/2007 | Zucherman et al. | | 2008/0051785 A1 | 2/2008 | Zucherman et al. |
| 2007/0203497 A1 | 8/2007 | Zucherman et al. | | 2008/0051898 A1 | 2/2008 | Zucherman et al. |
| 2007/0203501 A1 | 8/2007 | Zucherman et al. | | 2008/0051899 A1 | 2/2008 | Zucherman et al. |
| 2007/0208345 A1 | 9/2007 | Marnay et al. | | 2008/0051904 A1 | 2/2008 | Zucherman et al. |
| 2007/0208346 A1 | 9/2007 | Marnay et al. | | 2008/0051905 A1 | 2/2008 | Zucherman et al. |
| 2007/0208347 A1 | 9/2007 | Zucherman et al. | | 2008/0058806 A1 | 3/2008 | Klyce et al. |
| 2007/0208366 A1 | 9/2007 | Pellegrino et al. | | 2008/0058807 A1 | 3/2008 | Klyce et al. |
| 2007/0213724 A1 | 9/2007 | Arnin et al. | | 2008/0058808 A1 | 3/2008 | Klyce et al. |
| 2007/0213829 A1 | 9/2007 | Le Couedic et al. | | 2008/0058941 A1 | 3/2008 | Zucherman et al. |
| 2007/0219552 A1 | 9/2007 | Zucherman et al. | | 2008/0065086 A1 | 3/2008 | Zucherman et al. |
| 2007/0225706 A1 | 9/2007 | Clark et al. | | 2008/0065212 A1 | 3/2008 | Zucherman et al. |
| 2007/0225724 A1 | 9/2007 | Edmond | | 2008/0065213 A1 | 3/2008 | Zucherman et al. |
| 2007/0225807 A1 | 9/2007 | Phan et al. | | 2008/0065214 A1 | 3/2008 | Zucherman et al. |
| 2007/0225814 A1 | 9/2007 | Atkinson et al. | | 2008/0071378 A1 | 3/2008 | Zucherman et al. |
| 2007/0233068 A1 | 10/2007 | Bruneau et al. | | 2008/0086212 A1 | 4/2008 | Zucherman et al. |
| 2007/0233074 A1 | 10/2007 | Anderson et al. | | 2008/0167655 A1 | 7/2008 | Wang et al. |
| 2007/0233076 A1 | 10/2007 | Trieu | | 2008/0167656 A1 | 7/2008 | Zucherman et al. |
| 2007/0233077 A1 | 10/2007 | Khalili | | 2008/0167657 A1 | 7/2008 | Greenhalgh |
| 2007/0233081 A1 | 10/2007 | Pasquet et al. | | 2008/0172057 A1 | 7/2008 | Zucherman et al. |
| 2007/0233082 A1 | 10/2007 | Chin et al. | | 2008/0177272 A1 | 7/2008 | Zucherman et al. |
| 2007/0233083 A1 | 10/2007 | Abdou | | 2008/0183210 A1 | 7/2008 | Zucherman et al. |
| 2007/0233084 A1 | 10/2007 | Betz et al. | | 2008/0188895 A1 | 8/2008 | Cragg et al. |
| 2007/0233088 A1 | 10/2007 | Edmond | | 2008/0188941 A1 | 8/2008 | Grotz |
| 2007/0233089 A1 | 10/2007 | DiPoto et al. | | 2008/0195152 A1 | 8/2008 | Altarac et al. |
| 2007/0233096 A1 | 10/2007 | Garcia-Bengochea | | 2008/0208344 A1 | 8/2008 | Kilpela et al. |
| 2007/0233098 A1 | 10/2007 | Mastrorio et al. | | 2008/0215058 A1 | 9/2008 | Zucherman et al. |
| 2007/0233129 A1 | 10/2007 | Bertagnoli et al. | | 2008/0215094 A1 | 9/2008 | Taylor |
| 2007/0239279 A1 | 10/2007 | Francis | | 2008/0221692 A1 | 9/2008 | Zucherman et al. |
| 2007/0250060 A1 | 10/2007 | Anderson et al. | | 2008/0228225 A1 | 9/2008 | Trautwein et al. |
| 2007/0260245 A1 | 11/2007 | Malandain et al. | | 2008/0234824 A1 | 9/2008 | Youssef et al. |
| 2007/0265623 A1 | 11/2007 | Malandain et al. | | 2008/0287997 A1 | 11/2008 | Altarac et al. |
| 2007/0265624 A1 | 11/2007 | Zucherman et al. | | 2008/0288075 A1 | 11/2008 | Zucherman et al. |
| 2007/0265625 A1 | 11/2007 | Zucherman et al. | | 2008/0319550 A1 | 12/2008 | Altarac et al. |
| 2007/0265626 A1 | 11/2007 | Seme | | 2009/0118833 A1 | 5/2009 | Hudgins et al. |
| 2007/0270812 A1 | 11/2007 | Peckham | | 2009/0125030 A1 | 5/2009 | Tebbe et al. |
| 2007/0270822 A1 | 11/2007 | Heinz | | 2009/0138046 A1 | 5/2009 | Altarac et al. |
| 2007/0270823 A1 | 11/2007 | Trieu et al. | | 2009/0138055 A1 | 5/2009 | Altarac et al. |
| 2007/0270824 A1 | 11/2007 | Lim et al. | | 2009/0248079 A1 | 10/2009 | Kwak et al. |
| 2007/0270825 A1 | 11/2007 | Carls et al. | | 2009/0292315 A1 | 11/2009 | Trieu |
| 2007/0270826 A1 | 11/2007 | Trieu et al. | | 2010/0042217 A1 | 2/2010 | Zucherman et al. |
| 2007/0270827 A1 | 11/2007 | Lim et al. | | 2010/0082108 A1 | 4/2010 | Zucherman et al. |
| 2007/0270828 A1 | 11/2007 | Bruneau et al. | | 2010/0262243 A1 | 10/2010 | Zucherman et al. |
| 2007/0270829 A1 | 11/2007 | Carls et al. | | 2010/0305611 A1 | 12/2010 | Zucherman et al. |
| 2007/0270834 A1 | 11/2007 | Bruneau et al. | | | | |
| 2007/0270840 A1 | 11/2007 | Chin et al. | | | | |

FOREIGN PATENT DOCUMENTS

| | | | |
|---|---|---|---|
| 2007/0272259 A1 | 11/2007 | Allard et al. | |
| 2007/0276368 A1 | 11/2007 | Trieu et al. | EP 322334 B1 2/1992 |
| 2007/0276369 A1 | 11/2007 | Allard et al. | EP 767636 B1 1/1999 |
| 2007/0276370 A1 | 11/2007 | Altarac et al. | EP 768843 B1 2/1999 |
| 2007/0276372 A1 | 11/2007 | Malandain et al. | EP 1027004 A1 8/2000 |
| 2007/0276373 A1 | 11/2007 | Malandain | EP 1030615 A1 8/2000 |
| 2007/0276493 A1 | 11/2007 | Malandain et al. | EP 1138268 A1 10/2001 |
| 2007/0276496 A1 | 11/2007 | Lange et al. | EP 1330987 A1 7/2003 |
| 2007/0276497 A1 | 11/2007 | Anderson | EP 1056408 B1 12/2003 |
| 2007/0276500 A1 | 11/2007 | Zucherman et al. | EP 1343424 B1 9/2004 |
| 2008/0015700 A1 | 1/2008 | Zucherman et al. | EP 1454589 A1 9/2004 |
| 2008/0021468 A1 | 1/2008 | Zucherman et al. | EP 1148850 B1 4/2005 |
| 2008/0021560 A1 | 1/2008 | Zucherman et al. | EP 1299042 B1 3/2006 |
| | | | EP 1578314 B1 5/2007 |

| | | | |
|---|---|---|---|
| EP | 1675535 B1 | 5/2007 | |
| EP | 959792 B1 | 11/2007 | |
| WO | 9404088 A1 | 3/1994 | |
| WO | 9426192 A1 | 11/1994 | |
| WO | 9525485 A1 | 9/1995 | |
| WO | 9531158 A1 | 11/1995 | |
| WO | 9600049 A1 | 1/1996 | |
| WO | 9829047 A1 | 7/1998 | |
| WO | 9921500 A1 | 5/1999 | |
| WO | 9921501 C2 | 8/1999 | |
| WO | 9942051 A1 | 8/1999 | |
| WO | WO-0013619 A1 | 3/2000 | |
| WO | 0044319 A1 | 8/2000 | |
| WO | 0044321 A2 | 12/2000 | |
| WO | 0128442 A1 | 4/2001 | |
| WO | 0191657 A1 | 12/2001 | |
| WO | 0191658 A1 | 12/2001 | |
| WO | 0203882 A2 | 1/2002 | |
| WO | 0207623 A1 | 1/2002 | |
| WO | 0207624 A1 | 1/2002 | |
| WO | 02051326 A1 | 7/2002 | |
| WO | 02071960 A1 | 9/2002 | |
| WO | WO-02067793 A2 | 9/2002 | |
| WO | WO-02076336 A2 | 10/2002 | |
| WO | 03007791 A2 | 1/2003 | |
| WO | 03007829 A1 | 1/2003 | |
| WO | 03008016 A2 | 1/2003 | |
| WO | 03015646 A2 | 2/2003 | |
| WO | 03045262 A2 | 6/2003 | |
| WO | 03099147 A1 | 12/2003 | |
| WO | 03101350 A1 | 12/2003 | |
| WO | 03024298 C2 | 6/2004 | |
| WO | WO-2004073533 A1 | 9/2004 | |
| WO | 2004110300 A2 | 12/2004 | |
| WO | 2005013839 A2 | 2/2005 | |
| WO | WO-2005009300 A1 | 2/2005 | |
| WO | 2005025461 A2 | 3/2005 | |
| WO | 2005041799 A1 | 5/2005 | |
| WO | 2005044152 A1 | 5/2005 | |
| WO | 2005055868 A2 | 6/2005 | |
| WO | 2005079672 A2 | 9/2005 | |
| WO | 2005115261 A1 | 12/2005 | |
| WO | 2006033659 A2 | 3/2006 | |
| WO | 2006034423 A2 | 3/2006 | |
| WO | 2006039260 A2 | 4/2006 | |
| WO | WO-2006039243 | 4/2006 | |
| WO | 2006045094 C2 | 6/2006 | |
| WO | 2006063047 A2 | 6/2006 | |
| WO | 2006065774 A1 | 6/2006 | |
| WO | 2006102269 A2 | 9/2006 | |
| WO | 2006102428 A1 | 9/2006 | |
| WO | 2006102485 A2 | 9/2006 | |
| WO | 2006107539 A1 | 10/2006 | |
| WO | 2006110462 A2 | 10/2006 | |
| WO | 2006110464 A1 | 10/2006 | |
| WO | 2006110767 A1 | 10/2006 | |
| WO | 2006113080 A2 | 10/2006 | |
| WO | 2006113406 A2 | 10/2006 | |
| WO | 2006113814 A2 | 10/2006 | |
| WO | 2006119235 A1 | 11/2006 | |
| WO | 2006119236 A2 | 11/2006 | |
| WO | 2006118945 C1 | 12/2006 | |
| WO | 2006135511 A1 | 12/2006 | |
| WO | 2007015028 A1 | 2/2007 | |
| WO | 2007035120 A1 | 3/2007 | |
| WO | 2007075375 A2 | 7/2007 | |
| WO | 2007075788 A2 | 7/2007 | |
| WO | 2007075791 A2 | 7/2007 | |
| WO | 2007089605 A2 | 8/2007 | |
| WO | 2007089905 A2 | 8/2007 | |
| WO | 2007089975 A1 | 8/2007 | |
| WO | 2007097735 A2 | 8/2007 | |
| WO | 2007109402 A2 | 9/2007 | |
| WO | 2007110604 A1 | 10/2007 | |
| WO | 2007111795 A1 | 10/2007 | |
| WO | 2007111979 A2 | 10/2007 | |
| WO | 2007111999 A2 | 10/2007 | |
| WO | 2007117882 A1 | 10/2007 | |
| WO | 2007121070 A2 | 10/2007 | |
| WO | 2007127550 A2 | 11/2007 | |
| WO | 2007127588 A1 | 11/2007 | |
| WO | 2007127677 A1 | 11/2007 | |
| WO | 2007127689 A2 | 11/2007 | |
| WO | 2007127694 A2 | 11/2007 | |
| WO | 2007127734 A2 | 11/2007 | |
| WO | 2007127736 A2 | 11/2007 | |
| WO | 2007131165 A2 | 11/2007 | |
| WO | 2007134113 A2 | 11/2007 | |
| WO | WO-2008048645 A2 | 4/2008 | |

OTHER PUBLICATIONS

Non-Final Office Action; U.S. Appl. No. 11/006,502; Mailing Date: Nov. 7, 2008, 7 pages.
Final Office Action; U.S. Appl. No. 11/006,521; Mailing Date: May 17, 2010, 10 pages.
Final Office Action; U.S. Appl. No. 11/006,521; Mailing Date: Dec. 5, 2008, 10 pages.
Final Office Action; U.S. Appl. No. 11/052,002; Mailing Date: Apr. 1, 2009, 7 pages.
Final Office Action; U.S. Appl. No. 11/079,006; Mailing Date: Nov. 10, 2009, 7 pages.
Final Office Action; U.S. Appl. No. 11/190,496; Mailing Date: May 19, 2009, 8 pages.
Final Office Action; U.S. Appl. No. 11/305,820; Mailing Date: Jun. 16, 2008, 9 pages.
Final Office Action; U.S. Appl. No. 11/314,712; Mailing Date: Sep. 4, 2009, 9 pages.
International Search Report and Written Opinion; Application No. PCT/US2005/038026; Mailing Date: Apr. 22, 2008, 9 pages.
International Search Report and Written Opinion; Application No. PCT/US2005/044256; Mailing Date: Jul. 28, 2006, 7 pages.
International Search Report and Written Opinion; Application No. PCT/US2006/047824; Mailing Date: Oct. 16, 2008, 3 pages.
International Search Report and Written Opinion; Application No. PCT/US2006/048611; Mailing Date: Oct. 14, 2008; 10 pages.
International Search Report and Written Opinion; Application No. PCT/US2006/048614; Mailing Date: Feb. 3, 2006; 23 pages.
International Search Report and Written Opinion; Application No. PCT/US2007/022171; Mailing Date: Apr. 15, 2008, 13 pages.
International Search Report and Written Opinion; Application No. PCT/US2007/023312; Mailing Date: May 22, 2008, 14 pages.
International Search Report and Written Opinion; Application No. PCT/US2008/004901; Mailing Date: Aug. 19, 2008, 7 pages.
International Search Report and Written Opinion; Application No. PCT/US2008/075487; Mailing Date: Dec. 31, 2008, 7 pages.
Non-Final Office Action; U.S. Appl. No. 10/970,843; Mailing Date: Aug. 29, 2008, 9 pages.
Non-Final Office Action; U.S. Appl. No. 10/970,843; Mailing Date: Oct. 8, 2009, 8 pages.
Non-Final Office Action; U.S. Appl. No. 11/006,521; Mailing Date: Feb. 28, 2008, 13 pages.
Non-Final Office Action; U.S. Appl. No. 11/006,521; Mailing Date: Aug. 26, 2009, 9 pages.
Non-Final Office Action; U.S. Appl. No. 11/052,002; Mailing Date: Sep. 18, 2007, 7 pages.
Non-Final Office Action; U.S. Appl. No. 11/052,002; Mailing Date: Dec. 24, 2009, 6 pages.
Non-Final Office Action; U.S. Appl. No. 11/079,006; Mailing Date: Jan. 30, 2009, 7 pages.
Non-Final Office Action; U.S. Appl. No. 11/079,006; Mailing Date: Sep. 18, 2007, 6 pages.
Non-Final Office Action; U.S. Appl. No. 11/190,496; Mailing Date: Aug. 25, 2008, 6 pages.
Non-Final Office Action; U.S. Appl. No. 11/190,496; Mailing Date: Oct. 31, 2007, 7 pages.
Non-Final Office Action; U.S. Appl. No. 11/305,820; Mailing Date: Oct. 9, 2007, 8 pages.
Non-Final Office Action; U.S. Appl. No. 11/314,712; Mailing Date: Jan. 21, 2009, 8 pages.
Non-Final Office Action; U.S. Appl. No. 11/582,874; Mailing Date: Jan. 4, 2010, 9 pages.

Non-Final Office Action; U.S. Appl. No. 11/593,995; Mailing Date: Apr. 19, 2010, 10 pages.
Supplementary European Search Report; Application No. EP05849654.8; Applicant: Vertiflex, Inc; Date of Completion: May 15, 2009, 10 pages.
Supplementary European Search Report; Application No. EP07861721.4; Applicant: Vertiflex, Inc; Date of Completion: Nov. 24, 2009, 6 pages.
Supplementary European Search Report; Application No. EP09170304.1; Applicant: Vertiflex, Inc; Date of Completion: Nov. 11, 2009, 5 pages.
Supplementary European Search Report; Application No. EP09170338.9; Applicant: Vertiflex, Inc; Date of Completion: Nov. 12, 2009, 6 pages.
Swan, Colby, "Preliminary Design and Experimental Studies of a Novel Soft Implant for Correcting Sogittal Plane Instability in the Lumbar Spine," Spine, 1997, 22(16), 1826-1827.
Final Office Action; U.S. Appl. No. 10/970,843; Mailing Date: Feb. 12, 2009, 7 pages.
Final Office Action; U.S. Appl. No. 10/970,843; Mailing Date: Jul. 2, 2010, 9 pages.
Final Office Action; U.S. Appl. No. 11/052,002; Mailing Date: Sep. 1, 2010, 7 pages.
Final Office Action; U.S. Appl. No. 11/582,874; Mailing Date: Sep. 10, 2010, 10 pages.
Non-Final Office Action; U.S. Appl. No. 12/338,793; Mailing Date: Sep. 21, 2010, 9 pages.
European Office Action Application No. EP05849654.8; Applicant: The Board of Trustees of the Leland Stanford Junior University; Date of Completion: Jun. 21, 2011, 4 pages.
Non-Final Office Action; U.S. Appl. No. 12/205,511 Mailing Date: Apr. 20, 2011 9 pages.
Non-Final Office Action; U.S. Appl. No. 12/358,010 Mailing Date: Jul. 14, 2011; 9 pages.
Supplementary European Search Report; Application No. EP07861426.0; Applicant: Vertiflex, Inc; Date of Completion: Jun. 7, 2011, 6 pages.
Supplementary European Search Report; Application No. EP09702116.6; Applicant: Vertiflex, Inc; Date of Completion: Feb. 11, 2011, 6 pages.
Supplementary European Search Report; Application No. EP11151901.3; Applicant: Vertiflex, Inc; Date of Completion: Apr. 7, 2011, 6 pages.
International Search Report and Written Opinion for application No. PCT/US2008/087527, Mail Date Jul. 30, 2009, 15 pages.
International Search Report and Written Opinion for application No. PCT/US2008/008983, Mail Date Feb. 23, 2009, 10 pages.
Minns R.J. et al., "Preliminary Design and Experiment Studies of a Novel Soft Implant for Correcting Sagittal Plane Instability in the Lumbar Spine," Spine, 1997, 22(16), 1819-1827.
International Search Report and Written Opinion for application No. PCT/US2008/008382, Mail Date Mar. 2, 2009, 16 pages.
International Search Report and Written Opinion for application No. PCT/US09/031710, Mail Date Sep. 1, 2009,10 pages.
International Search Report and Written Opinion for application No. PCT/US09/031150, Mail Date Aug. 28, 2009, 7 pages.
International Search Report and Written Opinion for application No. PCT/US09/036561, Mail Date Sep. 17, 2009, 12 pages.

* cited by examiner

SECTION A-A

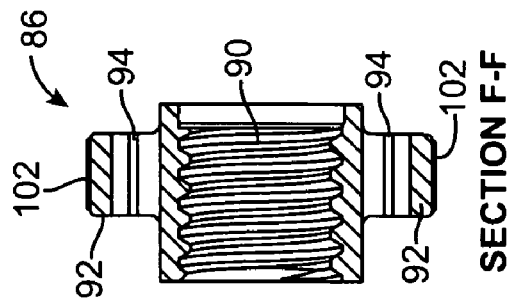
FIG. 4c
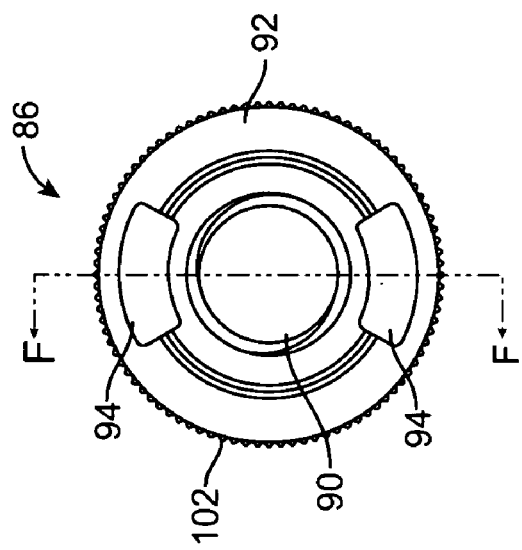
FIG. 4b
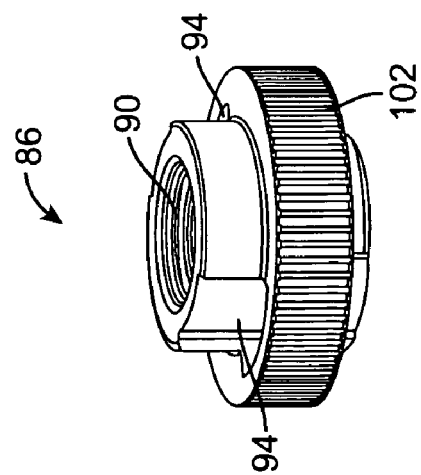
FIG. 4a
FIG. 4e
FIG. 4d

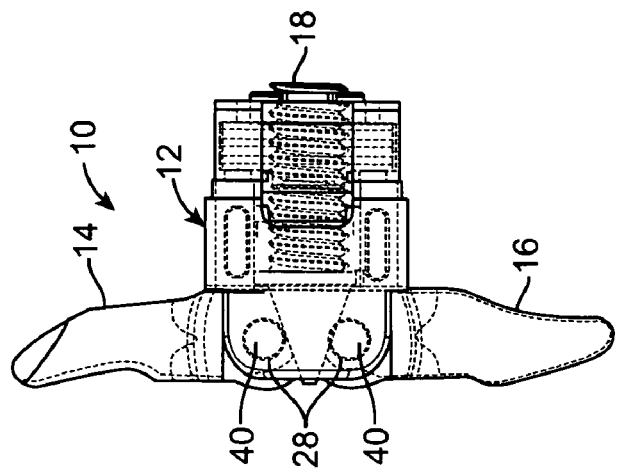
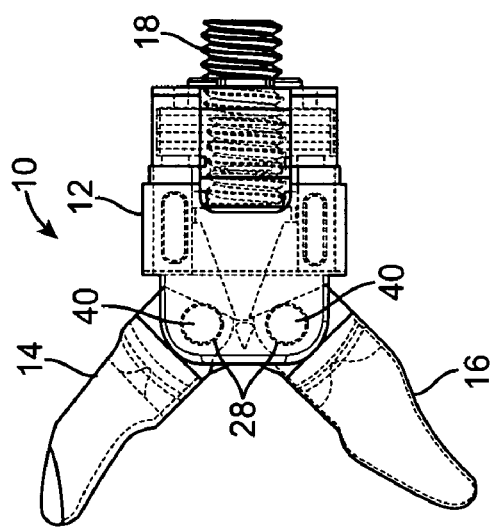
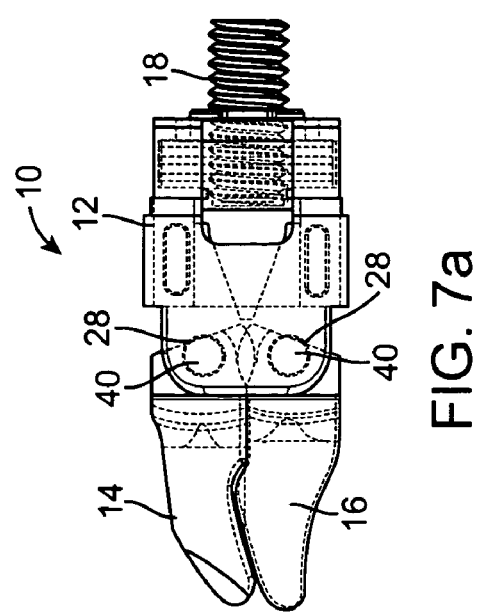
FIG. 7c
FIG. 7b
FIG. 7a

INTERSPINOUS SPACER

CROSS-REFERENCE TO RELATED APPLICATIONS

This application claims priority to and the benefit of and is a continuation-in-part of U.S. Provisional Patent Application Ser. No. 60/961,741 entitled "Interspinous spacer" filed on Jul. 24, 2007 which is incorporated herein by reference in its entirety. This application also claims priority to and is a continuation-in-part of U.S. patent application Ser. No. 12/217,662 entitled "Interspinous spacer" filed on Jul. 8, 2008 which is a non-provisional of U.S. Provisional Patent Application No. 60/958,876 entitled "Interspinous spacer" filed on Jul. 9, 2007 and a continuation-in-part of U.S. patent application Ser. No. 12/148,104 entitled "Interspinous spacer" filed on Apr. 16, 2008 which is a non-provisional of U.S. Provisional Patent Application Ser. No. 60/923,971 entitled "Interspinous spacer" filed on Apr. 17, 2007 and U.S. Provisional Patent Application Ser. No. 60/923,841 entitled "Spacer insertion instrument" filed on Apr. 16, 2007, all of which are hereby incorporated by reference in their entireties. This application is also a continuation-in-part of U.S. patent application Ser. No. 11/593,995 entitled "Systems and methods for posterior dynamic stabilization of the spine" filed on Nov. 7, 2006 which is a continuation-in-part of U.S. patent application Ser. No. 11/582,874 entitled "Minimally invasive tooling for delivery of interspinous spacer" filed on Oct. 18, 2006, now U.S. Pat. No. 8,128,662 which is a continuation-in-part of U.S. patent application Ser. No. 11/314,712 entitled "Systems and methods for posterior dynamic stabilization of the spine" filed on Dec. 20, 2005, now U.S. Pat. No. 8,152,837 which is a continuation-in-part of U.S. patent application Ser. No. 11/190,496 entitled "Systems and methods for posterior dynamic stabilization of the spine" filed on Jul. 26, 2005 which is a continuation-in-part of U.S. patent application Ser. No. 11/079,006 entitled "Systems and methods for posterior dynamic stabilization of the spine" filed on Mar. 10, 2005, now U.S. Pat. No. 8,012,207 which is a continuation-in-part of U.S. patent application Ser. No. 11/052,002 entitled "Systems and methods for posterior dynamic stabilization of the spine" filed on Feb. 4, 2005 which is a continuation-in-part of U.S. patent application Ser. No. 11/006,502 entitled "Systems and methods for posterior dynamic stabilization of the spine" filed on Dec. 6, 2004, now U.S. Pat. No. 8,123,807 which is a continuation-in-part of U.S. patent application Ser. No. 10/970,843 entitled "Systems and methods for posterior dynamic stabilization of the spine" filed on Oct. 20, 2004, now U.S. Pat. No. 8,167,944, all of which are hereby incorporated by reference in their entireties.

FIELD

The present invention generally relates to medical devices, in particular, implants for placement between adjacent spinous processes of a patient's spine.

BACKGROUND

With spinal stenosis, the spinal canal narrows and pinches the spinal cord and nerves, causing pain in the back and legs. Typically, with age, a person's ligaments may thicken, intervertebral discs may deteriorate and facet joints may break down-all contributing to the condition of the spine characterized by a narrowing of the spinal canal. Injury, heredity, arthritis, changes in blood flow and other causes may also contribute to spinal stenosis.

Doctors have been at the forefront with various treatments of the spine including medications, surgical techniques and implantable devices that alleviate and substantially reduce debilitating pain associated with the back. In one surgical technique, a spacer is implanted between adjacent interspinous processes of a patient's spine. The implanted spacer opens the spinal canal, maintains the desired distance between vertebral body segments, and as a result, avoids impingement of nerves and relieves pain. For suitable candidates, an implantable interspinous spacer may provide significant benefits in terms of pain relief.

Any surgery is an ordeal. However, the type of device and how it is implanted has an impact. For example, one consideration when performing surgery to implant an interspinous spacer is the size of the incision that is required to allow introduction of the device. Small incisions and minimally invasive techniques are generally preferred as they affect less tissue and result in speedier recovery times. As such, there is a need for interspinous spacers that work well with surgical techniques that are minimally invasive for the patient. The present invention sets forth such a spacer.

SUMMARY

According to one aspect of the invention, an implantable spacer for placement between adjacent spinous processes is provided. The spacer includes a body defining a longitudinal axis. A first arm and a second arm are connected to the body and capable of movement with respect to the body. Each arm defines a configuration for receiving a spinous process and has a proximal caming surface. The spacer further includes an actuator assembly connected to the body. The actuator assembly includes an actuator having at least one bearing surface, a shaft connected to the actuator and configured for movement with respect to the body; and a spindle. The actuator assembly is configured to move relative to the body such that rotation of the spindle moves the actuator such that the at least one bearing surface contacts at least one of the caming surfaces to move both of the arms from an undeployed configuration to a deployed configuration in which the arms receive adjacent spinous processes.

According to another aspect of the invention, an implantable spacer for placement between adjacent spinous processes is disclosed. The implant includes a body defining a longitudinal axis. A first arm and a second arm are both connected to the body and capable of movement with respect to the body. Each arm has a configuration for receiving a spinous process and each arm has a proximal caming surface. The spacer further includes an actuator connected to the body and configured to move relative to the body to deploy the arms from an undeployed configuration. In the deployed configuration, the arms seat adjacent spinous processes. The spacer also includes a lock configured to provide resistance to keep the arms in place.

According to another aspect of the invention, a spinal implant for relieving pain and implantable between a superior spinous process and an inferior spinous process is disclosed. The implant includes a body connected prior to implantation to at least one arm. The at least one arm is movable with respect to the body into at least one configuration that is adapted to laterally stabilize and secure the implant with respect to an adjacent spinous process. In one variation, the implant includes a first arm for laterally stabilizing the body with respect to the superior spinous process and a second arm for laterally stabilizing the body with respect to the inferior spinous process.

According to another aspect of the invention, a spinal implant for relieving pain and implantable between a superior spinous process and an inferior spinous process is disclosed. The implant includes a body connected prior to implantation to at least one arm. The at least one arm is movable with respect to the body into at least one configuration that is adapted to laterally stabilize and secure the body with respect to an adjacent spinous process. In one variation, the implant includes a first arm for laterally stabilizing the body with respect to the superior spinous process and a second arm for laterally stabilizing the body with respect to the inferior spinous process. The implant includes a collapsed configuration in which a first end of the first arm and a first end of the second arm form the leading edge of the implant.

According to another aspect of the invention, a spinal implant for relieving pain and implantable between a superior spinous process and an inferior spinous process is disclosed. The implant includes a body connected prior to implantation to at least one arm. The at least one arm is movable with respect to the body into at least one configuration that is adapted to laterally stabilize and secure the body with respect to an adjacent spinous process. In one variation, the implant includes a first arm for laterally stabilizing the body with respect to the superior spinous process and a second arm for laterally stabilizing the body with respect to the inferior spinous process. A second end of the first arm is hinged to the distal end of the body and a second end of the second arm is hinged to the distal end of the body. In one variation, the first and second arms are configured to rotate approximately 90 degrees about their hinged ends into a deployed configuration. In one variation, wherein when rotated approximately 90 degrees, the first and second arms are in a configuration that is adapted to laterally stabilize/secure the body with respect to adjacent spinous processes. In another variation, wherein after rotation of approximately 90 degrees, each of the first and second arms are configured to translate away from the body such that the arms are closer to their respective spinous processes.

BRIEF DESCRIPTION OF THE DRAWINGS

The invention is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity.

FIG. 4a illustrates a perspective view of a spindle of an actuator assembly of a spacer according to the present invention.

FIG. 4b illustrates a top view of a spindle of an actuator assembly of a spacer according to the present invention.

FIG. 4c illustrates a cross-sectional view of the spindle of FIG. 4b taken along line F-F according to the present invention.

FIG. 4d illustrates a perspective view of a lock according to the present invention.

FIG. 4e illustrates a top view of a lock according to the present invention.

FIG. 7a illustrates a side, semi-transparent view of a spacer in a closed undeployed configuration according to the present invention.

FIG. 7b illustrates a side, semi-transparent view of a spacer in a partially deployed configuration according to the present invention.

FIG. 7c illustrates a side, semi-transparent view of a spacer in a deployed configuration according to the present invention.

DETAILED DESCRIPTION

Figure 1A:
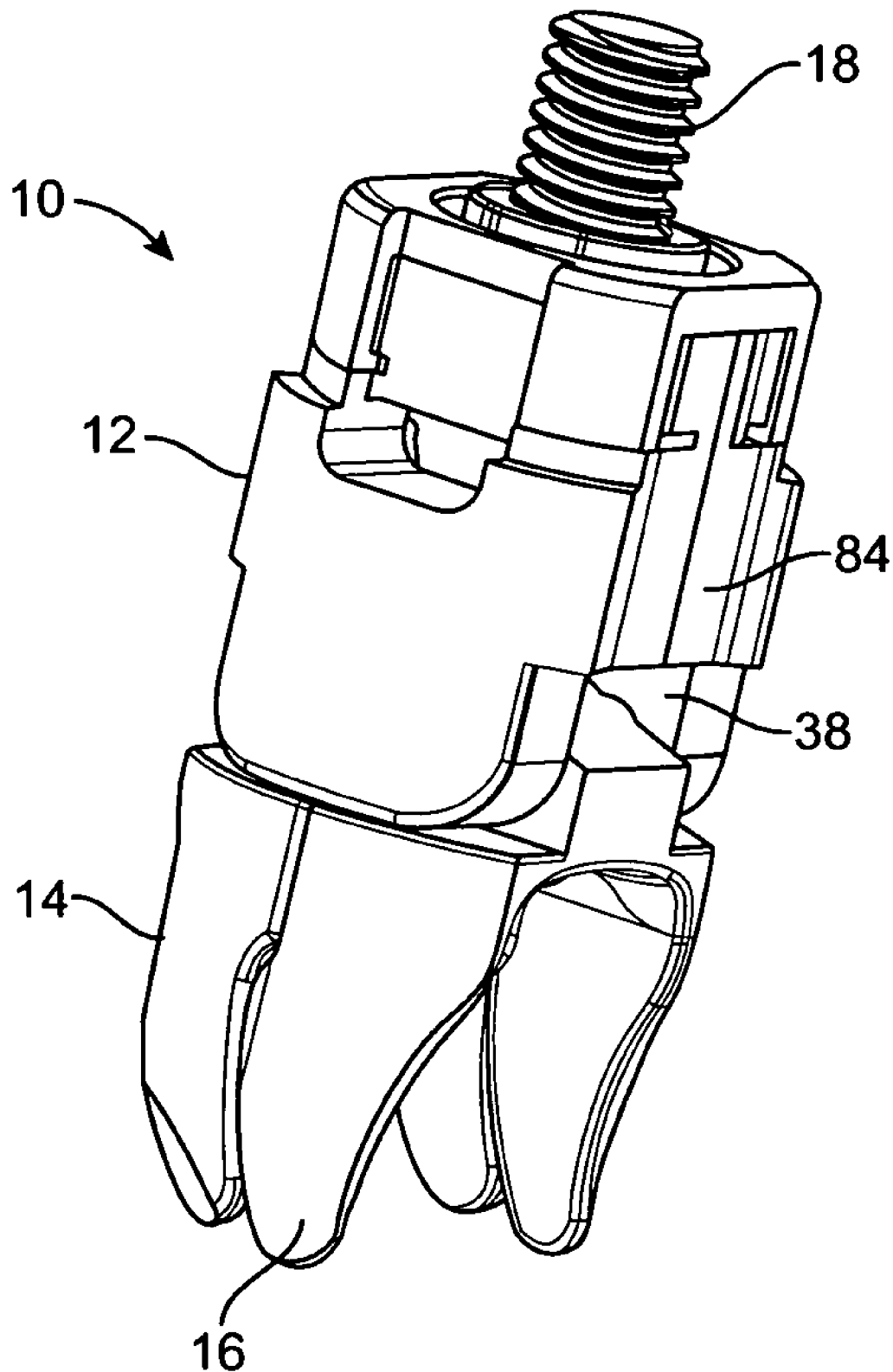
FIG. 1a illustrates a perspective view of a spacer according to the present invention.

Before the subject devices, systems and methods are described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs.

It must be noted that as used herein and in the appended claims, the singular forms "a", "an", and "the" include plural referents unless the context clearly dictates otherwise. Thus, for example, reference to "a spinal segment" may include a plurality of such spinal segments and reference to "the screw" includes reference to one or more screws and equivalents thereof known to those skilled in the art, and so forth.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

The present invention is described in the accompanying figures and text as understood by a person having ordinary skill in the field of spinal implants and implant delivery instrumentation.

With reference to FIGS. 1a-1f, various views of a spacer 10 according to the present invention are shown. The spacer 10 includes a body 12 connected to a superior extension member or arm 14, an inferior extension member or arm 16, and an actuator assembly 18.

Figure 2A:
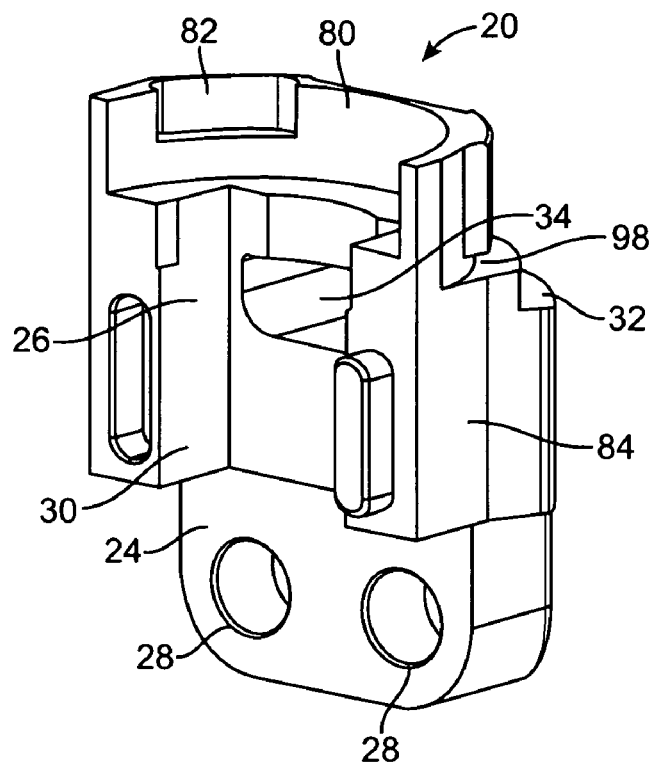
FIG. 2a illustrates a perspective view of half of a body of a spacer according to the present invention.
Figure 2B:
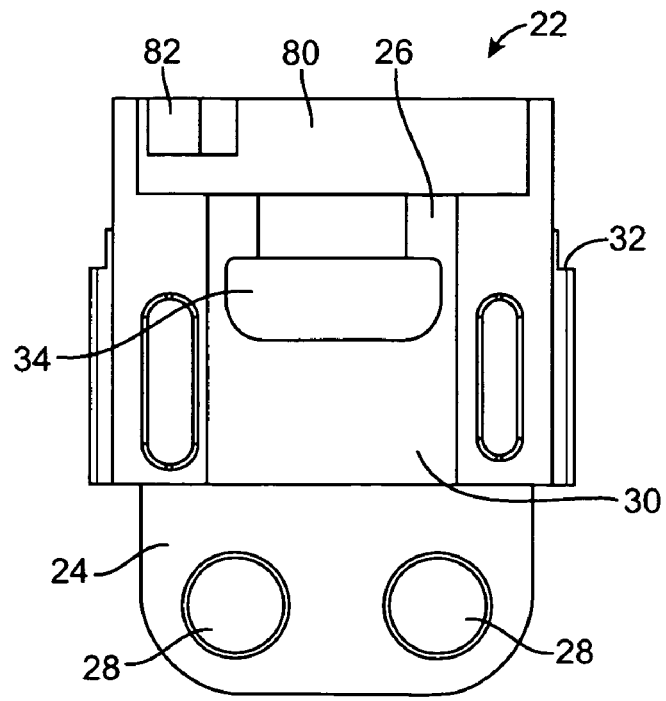
FIG. 2b illustrates a side view of half of a body of a spacer according to the present invention.

Turning now to FIGS. 2a-2b, the body 12 will now be described. The body 12 is shown to have a clamshell construction with a left body piece 20 (shown in FIG. 2a) joined to a right body piece 22 (shown in FIG. 2b) to capture arms 14, 16 inside. With the right and left body pieces 20, 22 joined together, the body 12 is generally cylindrical. The spacer body 12 has a cross-sectional size and shape that allows for implantation between adjacent spinous processes and facilitates delivery into a patient through a narrow port or cannula.

The inside of the body 12 defines an arm receiving portion 24 and an actuator assembly receiving portion 26 with features formed in each of the left and right body pieces 20, 22 that together define the arm and actuator assembly receiving portions 24, 26. In one variation, the arm receiving portion 24 includes slots or openings 28 that receive pins formed on the arms 14, 16 such that the pins rotate and/or translate inside the openings 28. The actuator assembly receiving portion 26 includes a passageway 30. The actuator assembly receiving portion 26 includes a spindle receiving portion 80 formed by the two joined pieces 20, 22 to form a ledge. The actuator assembly receiving portion 26 also includes at least one lock receiving portion 82. Other features include a tongue and groove for mating with the opposite clamshell.

Figure 1B:
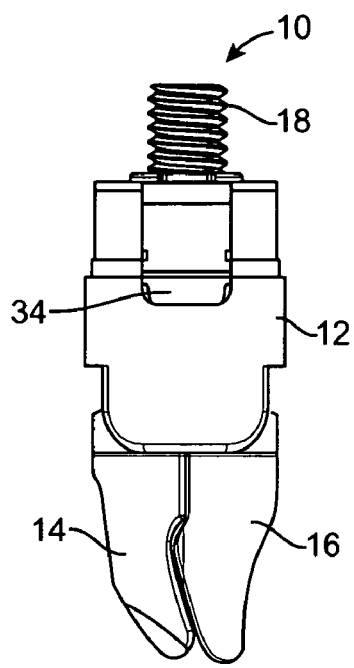
FIG. 1b illustrates a side view of a spacer according to the present invention.
Figure 1C:
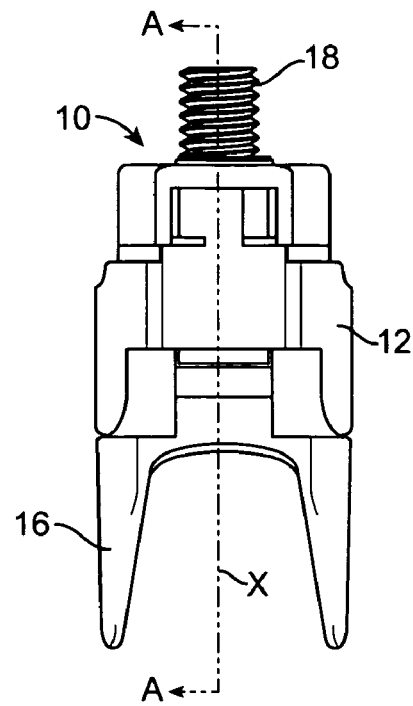
FIG. 1c illustrates a top view of a spacer according to the present invention.
Figure 1D:
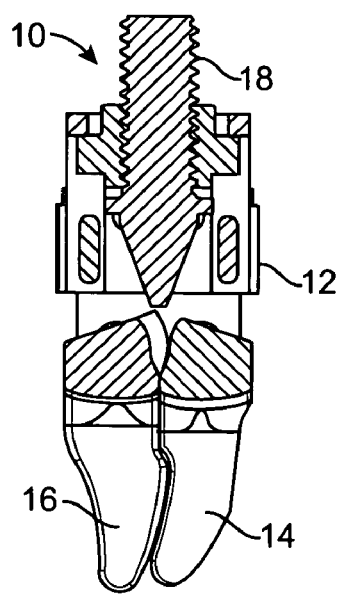
FIG. 1d illustrates a cross-sectional view of the spacer of FIG. 1c taken along line A-A according to the present invention.
Figure 1E:
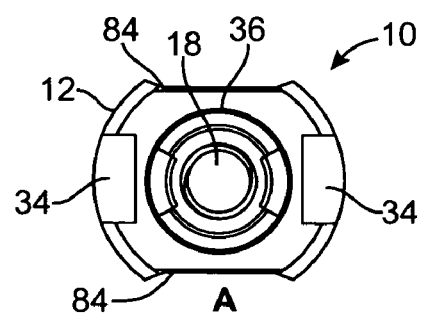
FIG. 1e illustrates an end view of a spacer according to the present invention.

The outside of the body 12 defines a ledge 32 along at least a portion of the periphery and at least one or continuous undercut 98. Notches 34 are formed at opposite locations as also shown in FIG. 1*b*. The notches 34 are configured for pronged attachment to a spacer delivery instrument. When joined together, the left and right body pieces 20, 22 define a proximal opening 36 (as seen in FIG. 1*e*) and a distal opening 38 (as seen in FIG. 1*a*) in the body 12. A longitudinal scallop 84 (also shown in FIGS. 1*a*, 1*e*, 1*f* and 2*a*) extending from the proximal end of the spacer to the distal end is formed in the outer surface of the body 12 to facilitate placement of the spacer 10 between and to conform to the anatomy of adjacent interspinous processes. On one variation, two oppositely located londigutinal scallops 84 are formed in the outer surface of the body 12 such that one scallop 84 faces the superior spinous process and the other scallop 84 faces the inferior spinous process. In one variation, the distance between oppositely located longitudinal scallops 84 (as best seen in FIG. 1*e*) is approximately 8.0 millimeters imparting the spacer 10 with a low profile advantageous for insertion between closely spaced or "kissing" spinous processes.

Figure 3A:
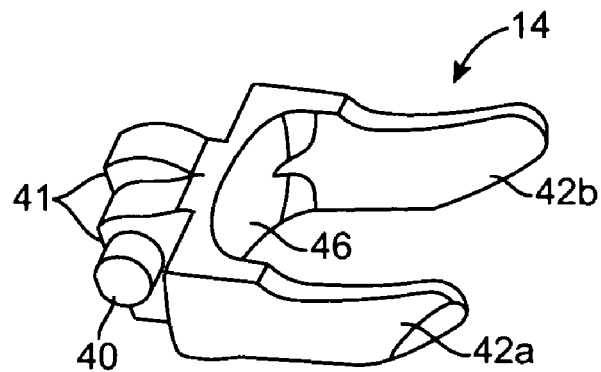
FIG. 3a illustrates a perspective view of a superior arm of a spacer according to the present invention.
Figure 3B:
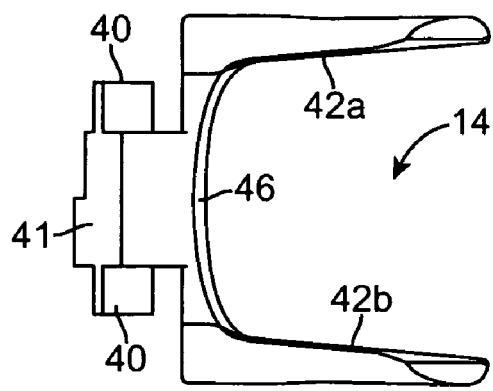
FIG. 3b illustrates a back view of a superior arm of a spacer according to the present invention.
Figure 3C:
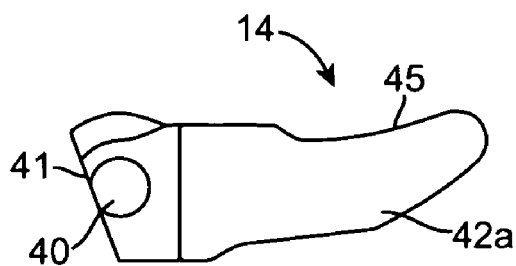
FIG. 3c illustrates a side view of a superior arm of a spacer according to the present invention.
Figure 3D:
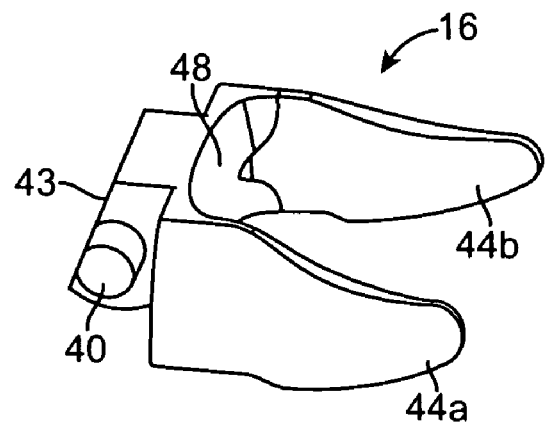
FIG. 3d illustrates a perspective view of an inferior arm of a spacer according to the present invention.
Figure 3E:
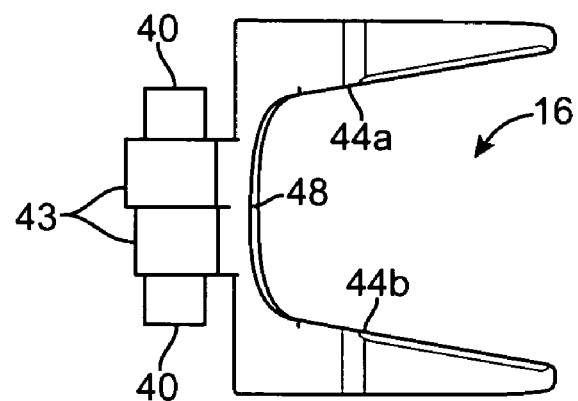
FIG. 3e illustrates a back view of an inferior arm of a spacer according to the present invention.
Figure 3F:
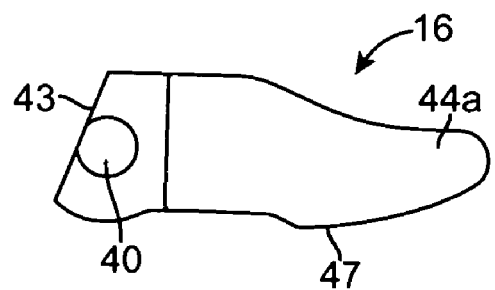
FIG. 3f illustrates a side view of an inferior arm of a spacer according to the present invention.

Turning now to FIGS. 3*a*-3*c*, the superior arm 14 is shown and in FIGS. 3*d*-3*f*, the inferior arm 16 is shown. The superior and inferior arms 14, 16 include pins 40 for mating with the body 12, in particular, for mating with the slots/openings 28 of the arm receiving portion 24. Each of the superior and inferior arms 14, 16 includes at least one caming surface 41, 43, respectively, for contact with the actuator assembly 18. The superior and inferior arms 14, 16 include elongated superior extensions 42*a*, 42*b* and elongated inferior extensions 44*a*, 44*b*, respectively. Extensions 42*a* and 44*a* are located on the left adjacent to the left body piece 20 and extensions 42*b* and 44*b* are located on right adjacent to the right body piece 22. Superior extensions 42*a*, 42*b* extend substantially parallel to each other in both an undeployed configuration and in a deployed configuration as do inferior extensions 44*a*, 44*b*. Extending between extensions 42*a*, 42*b* is a strut, bridge, bracket or saddle 46 that forms a superior substantially U-shaped configuration that is sized and configured to receive a superior spinous process. As seen in FIG. 3*c*, the anterior face of the superior extensions 14 includes a slight concavity or curvature 45 for conforming to the bony anatomy of the superior spinous process and or lamina. Extending between inferior extensions 44*a*, 44*b* is a strut, bridge, bracket or saddle 48 that forms an inferior substantially U-shaped configuration together with the extensions 44*a*, 44*b* that is sized and configured to receive an inferior spinous process of a spinal motion segment. As seen in FIG. 3*f*, the anterior face of the inferior extensions 16 includes a slight convexity or curvature 47 for conforming to the bony anatomy of the inferior spinous process and/or lamina. In one variation, the length of the saddle 46 of the superior arm 14 is approximately 8.5 millimeters and the length of the saddle 48 of the inferior arm 16 is approximately 6.6 millimeters. Also, the tip-to-tip distance of the superior extensions 42*a*, 42*b* is approximately 9.8 millimeters and the tip-to-tip distance of the inferior extensions 44*a*, 44*b* is approximately 9.4 millimeters. In sum, the seat comprising the saddle 46 and superior extensions 42*a*, 42*b* formed by the superior arm 14 is larger than the seat comprising the saddle 48 and inferior extensions 44*a*, 44*b* formed by the inferior arm 16. The larger superior seat of the spacer conforms closely to a wider lower end of the spinous process and the smaller inferior seat of the spacer conforms closely to a narrower upper end of the adjacent inferior spinous process when the spacer 10 is inserted between adjacent spinous processes as spinous processes are naturally narrower on top and wider on the bottom.

Figure 5C:
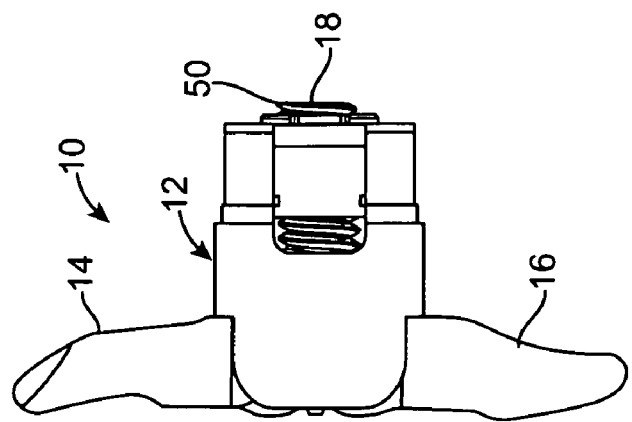
FIG. 5c illustrates a side view of a spacer in a deployed configuration according to the present invention.
Figure 5B:
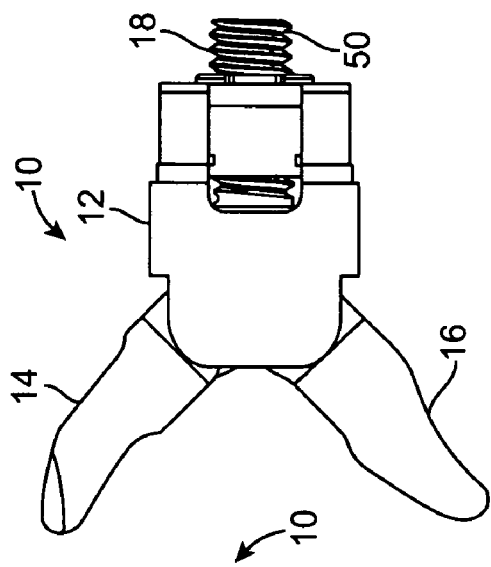
FIG. 5b illustrates a side view of a spacer in a partially deployed configuration according to the present invention.
Figure 5A:
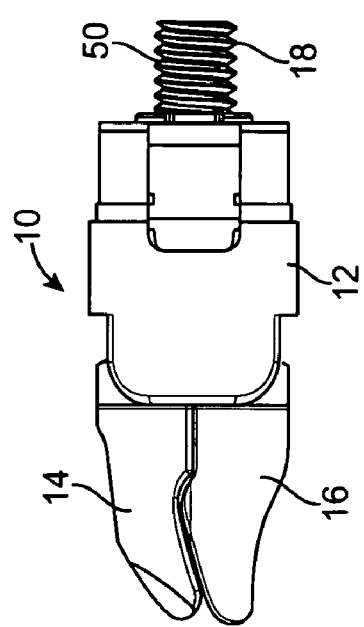
FIG. 5a illustrates a side view of a spacer in a closed, undeployed configuration according to the present invention.
Figure 6C:
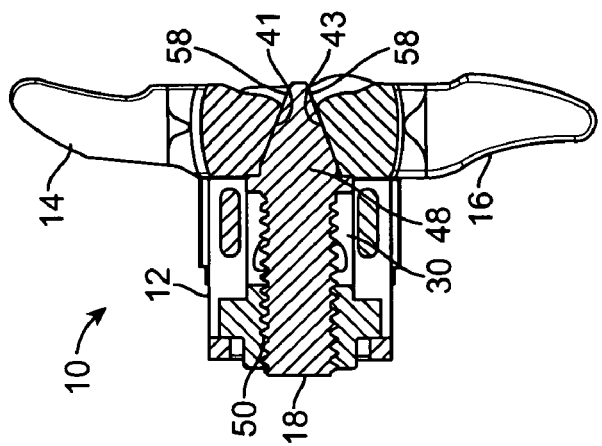
FIG. 6c illustrates a side, cross-sectional view of a spacer in a deployed configuration according to the present invention.
Figure 12A:
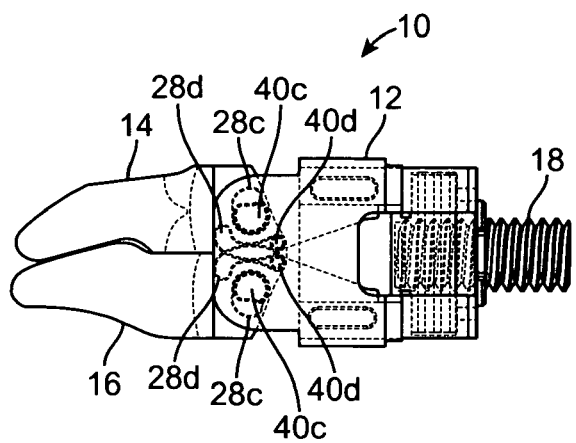
FIG. 12a illustrates a side, semi-transparent view of a spacer in a closed, undeployed configuration according to the present invention.
Figure 12B:
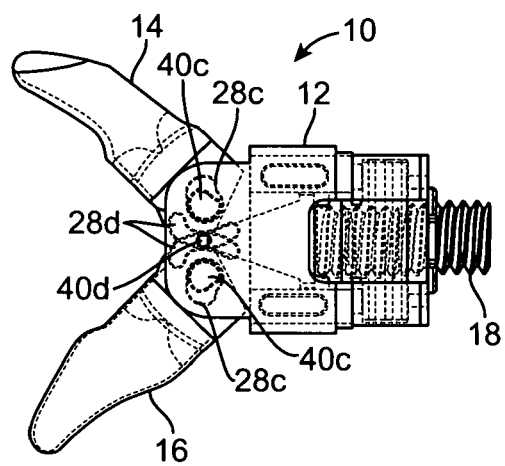
FIG. 12b illustrates a side, semi-transparent view of a spacer in a partially deployed configuration according to the present invention.
Figure 12C:
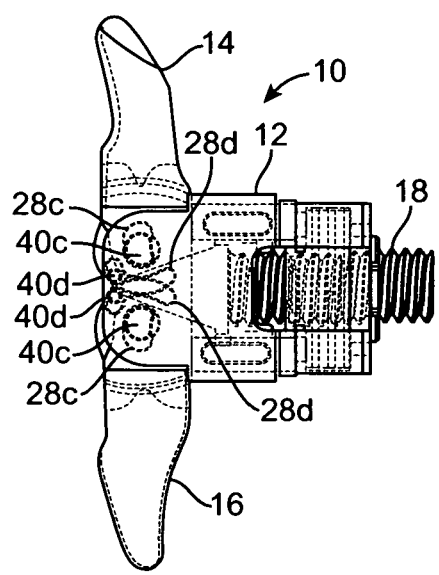
FIG. 12c illustrates a side, semi-transparent view of a spacer in a deployed configuration according to the present invention.
Figure 12D:
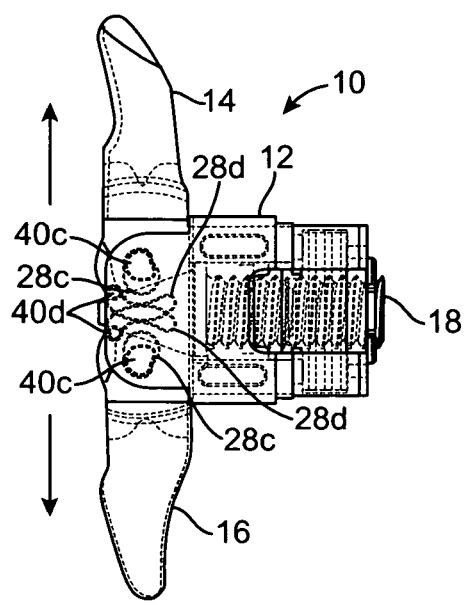
FIG. 12d illustrates a side, semi-transparent view of a spacer in a deployed and extended configuration according to the present invention.

The superior and inferior arms 14, 16 are movably or rotatably connected to the body 12, for example by hinge means or the like to provide rotational movement from an undeployed configuration to a deployed configuration that arcs through about a 90 degree range or more with respect to the body 12. The arms 14, 16 are rotationally movable between at least an undeployed, collapsed or folded state (as shown in FIGS. 1*a*-1*e*, 5*a*, 6*a* and 7*a*) and at least one deployed state (as shown in FIGS. 5*c*, 6*c*, 7*c*). In the undeployed state, the arm pairs 14, 16 are aligned generally or substantially axially (i.e., axially with the longitudinal axis, defined by the body 12 or to the translation path into the interspinous space of the patient) to provide a minimal lateral or radial profile. The longitudinal axis X of the spacer 10 and body 12 is shown in FIG. 1*c*. In the deployed state, the arm pairs 14, 16 are positioned such that each of the U-shaped saddles are in a plane (or planes) or have a U-shaped projection in a plane that is (are) generally or substantially transverse to the longitudinal axis X defined by the body 12 or to the collapsed position or to the implantation path into the interspinous space of the patient. In one variation, the spacer 10 is configured such that the arms 14, 16 are linearly moveable or translatable within the same transverse plane from a first deployed state (such as the state shown in FIG. 12*c*) to and from a second deployed state (such as the state shown in FIG. 12*d*) characterized by an additional translation of at least one of the arms 14, 16 with respect to the body 12 along a direction of the arrows as shown in FIG. 12*d* away from or towards the body 12. The arms 14, 16 can be extended in the general vertical direction along an axis along the general length of the spine wherein the arms 14, 16 are extended away from each other and away from the body 12 as denoted by the arrows in FIG. 12*d*. The arms 14, 16 can be un-extended in a direction towards each other and towards the body 12 for un-deployment or repositioning of the spacer 10. This feature advantageously allows for the most minimally invasive configuration for the spacer without compromising the ability of the spacer 10 to seat and contain the spinous processes in between levels where the anatomy of the spinous processes is such that the interspinous process space increases in the anterior direction or without compromising the ability of the spacer to provide adequate distraction. The arms 14, 16 are connected to the body 12 and/or to each other in a manner that enables them to be moved simultaneously or independently of each other, as well as in a manner that provides passive deployment and/or vertical extension or, alternatively, active or actuated deployment and/or vertical extension.

Figure 1F:
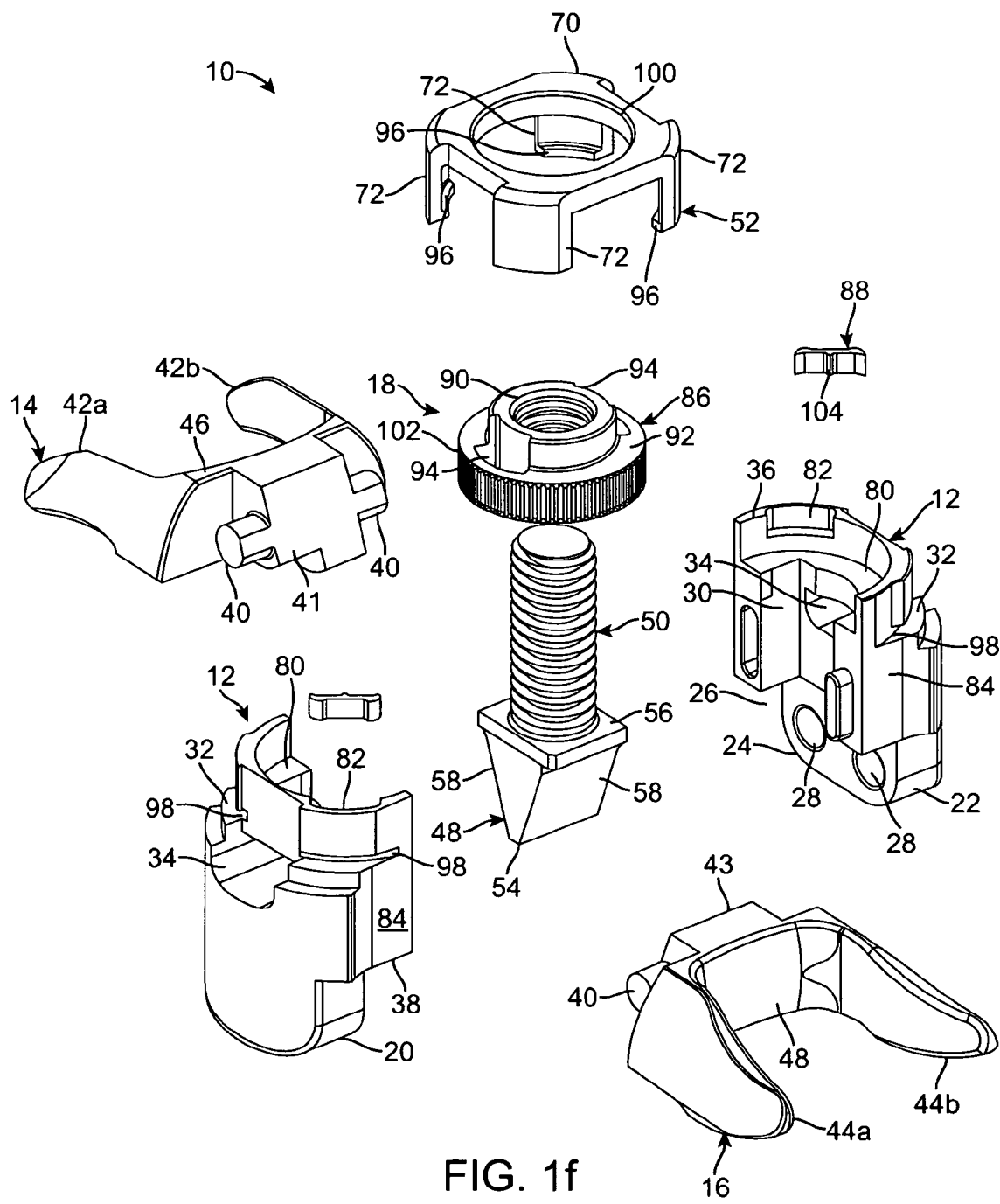
FIG. 1f illustrates an exploded perspective view of a spacer according to the present invention.

Turning back to FIG. 1*f*, the actuator assembly 18 will now be described. The actuator assembly 18 includes an actuator 48 connected to a shaft 50 and retainer 52, a spindle 86 and a optional lock 88. The actuator 48 includes a distal end 54 and a proximal end 56 and at least two bearing surfaces 58. The bearing surfaces 58 angle towards each other from the proximal end 56 to the distal end 54. In one variation as shown in FIG. 1*f*, the actuator 48 is integrally formed with the shaft 50. The shaft 50 is substantially cylindrical in shape and includes a threaded outer surface for engagement with a threaded inner surface of the spindle 86. The distal end 54 of the actuator 48 is further configured to engage the superior and inferior arms 14, 16 such that forward translation of the actuator 48 relative to the body 12 effects deployment of the arms into at least one deployed configuration.

Still referencing FIG. 1f and with particular reference to FIGS. 4a-4c, the spindle 86 has circular top profile and includes a central bore 90 having a threaded inner surface which is sized for threaded connection to the shaft 50. The spindle 86 includes an outer ledge 92 and oppositely disposed notches 94 for connecting to a deployment instrument. The outer sidewall of the spindle 86 includes a plurality of spindle teeth 102. The spindle 86 is configured to be disposed in the spindle receiving portion 80 of the body 12.

Still referencing FIG. 1f, the retainer 52, which is preferably made of metal such as surgical steel or titanium, includes a proximal end 70 and at least one prong 72 extending distally from the proximal end 70. Each prong 72 includes a hook portion 96 for hooking to the undercut 98 of the body 12 to attach the retainer 52 to the body 12. Each prong 72 is allowed to deflect and spring back to snap engage the undercut 98 and thereby connect to the body 12 and retain the actuator assembly 18 to the body 12. An aperture 100 is sized for clear passage of the actuator 48 and shaft 50. The actuator assembly 18 is at least partially disposed inside the body 12 and is configured to move with respect to the body 12.

Figure 4F:
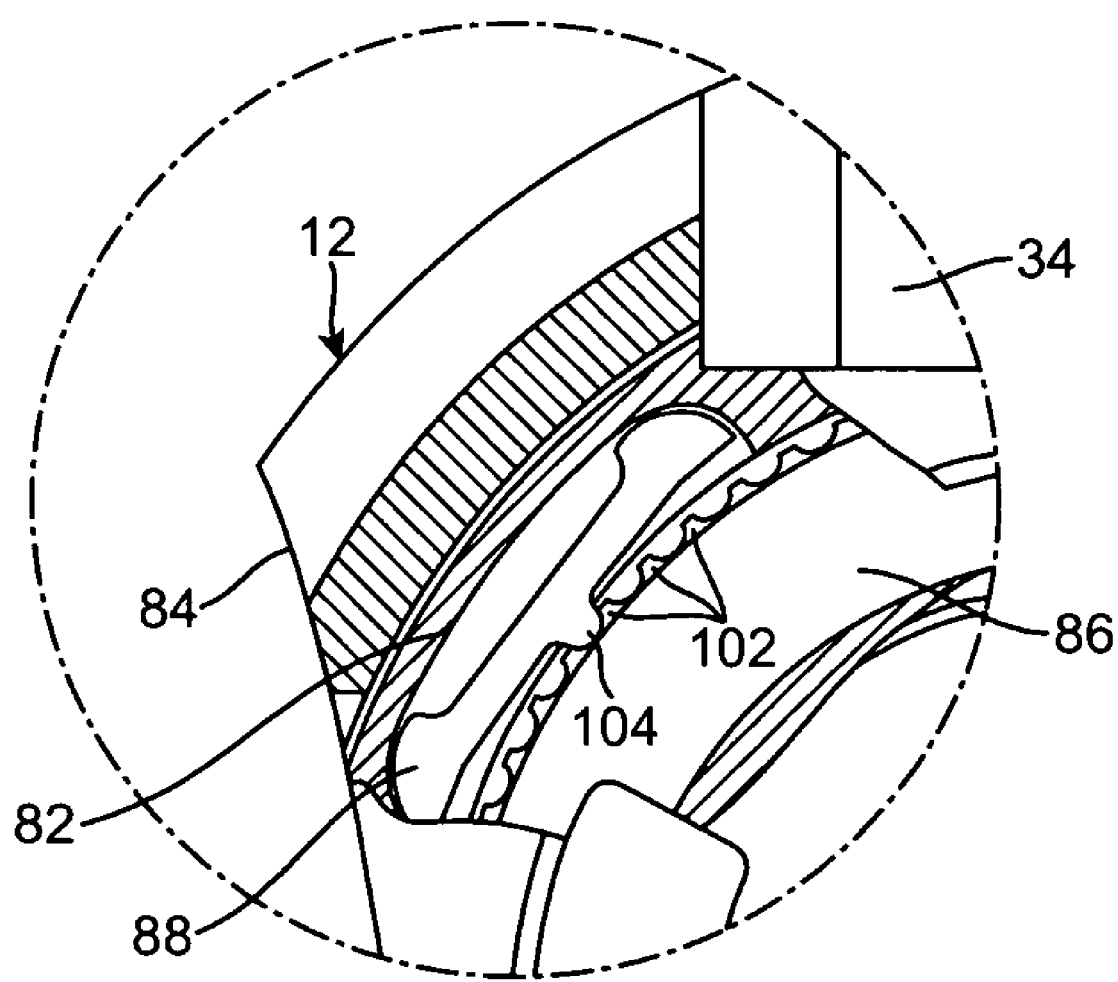
FIG. 4f illustrates a partial cross-sectional top view of a lock, body and spindle according to the present invention.

Still referencing FIG. 1f and with particular reference to FIGS. 4d, 4e and 4f, the lock 88 is a small elongate piece of metal or other suitable material such as steel or titanium capable of deflection. The lock 88 is sized to be disposed in the lock receiving portion 82 as shown in FIG. 4f. The lock 88 includes a tooth 104 which is configured to engage the spindle teeth 102. Rotation of the spindle 86 deflects the lock 88 outwardly which then snaps back into between the spindle teeth 102 to lock the spindle 86 in place.

Assembly of the spacer 10 with reference to FIGS. 1a-1f will now be described. The arms 14, 16 are disposed in the arm receiving portion 24 of one body piece. The other of the left or right body piece 20, 22 is securely connected/welded to the one body piece thereby capturing the arms 14, 16 inside the arm receiving portion 24 such that the arms 14, 16 are capable of at least rotational movement with respect to the body 12 and in one variation, capable of rotational movement and translation with respect to the body 12. In a variation in which the body 12 is made of one piece, the arms 14, 16 are movably connected to the body 12 with a pin, for example. The shaft 50 and the actuator 48 are together inserted into the proximal opening 36 and passageway 30 of the body 12. The spindle 86 is disposed in the spindle receiving portion 80 of the body 12 and threaded onto the shaft 50. The lock 88 is disposed inside the lock receiving portion 82 of the body 12. The retainer 52 is connected to the body 12 such that the hooked portion(s) 96 snap into the undercut(s) 98 and such that the shaft 50 can pass through the retainer aperture 100. The retainer 52 captures the spindle 86, actuator 48, shaft 50 and lock 88 inside the body 12 such that the spindle 86 is allowed to rotate and, thereby, move the actuator and shaft 48, 50 inside the body passageway 30.

Referring now to FIGS. 5a-5d, the spacer 10 is shown in a closed, undeployed configuration (FIG. 5a), a partially deployed configuration or otherwise intermediary configuration (FIG. 5b), and a deployed configuration (FIG. 5c). In moving from an undeployed to a deployed configuration, the actuator assembly 18 and, in particular, the shaft 50 of the actuator assembly moves distally with respect to the body to a position flush or almost flush with the proximal end of the body 12 or to a position completely inside the body 12 disappearing from sight providing a low profile for the spacer 10 along the longitudinal axis of the body 12.

Figure 6B:
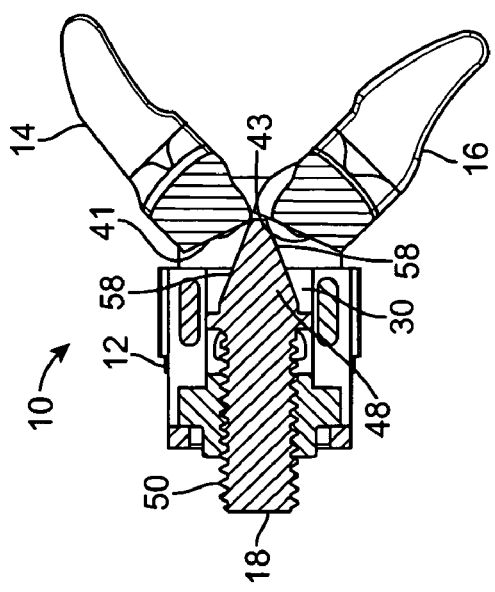
FIG. 6b illustrates a side, cross-sectional view of a spacer in a partially deployed configuration according to the present invention.
Figure 6A:
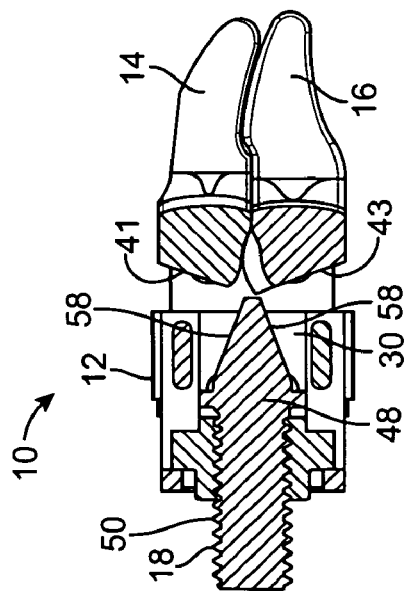
FIG. 6a illustrates a side, cross-sectional view of a spacer in a closed, undeployed configuration according to the present invention.

Turning now to the cross-sectional views of the spacer 10 in FIGS. 6a-6c, as the shaft 50 advances within the passageway 30, the bearing surfaces 58 of the actuator 48 contact the superior and inferior caming surfaces 41, 43 of the superior and inferior arms 14, 16 turning the arms 14, 16 into rotation with respect to the body 12. Upon rotation, the bearing surfaces 58 of the actuator 48 slide with respect to the superior and inferior caming surfaces 41, 43 of the superior and inferior arms 14, 16. The arms 14, 16 rotate through an arc of approximately 90 degrees with respect to the body 12 into the deployed configuration (FIG. 6c) in which the superior and inferior extensions of the arms 14, 16 are substantially perpendicular to the longitudinal axis of the spacer 10 as shown in FIG. 6c. The arms 14, 16 have a substantially U-shaped projection in a plane perpendicular to the longitudinal axis of the spacer 10.

Turning now to the semi-transparent views of the spacer 10 in FIGS. 7a-7c, the rotation of the pins 40 of the arms 14, 16 in the openings 28 of the body 12 is shown in moving from the configuration of FIG. 7a to the configuration of FIG. 7c. Reverse rotation of the spindle 86 moves the shaft 50 proximally with respect to the body 12 allowing the arms to close to any intermediary configuration between a deployed, configuration and an undeployed, closed configuration. This feature advantageously permits the surgeon to ease installation and positioning of the spacer with respect to patient anatomy.

Figure 8:
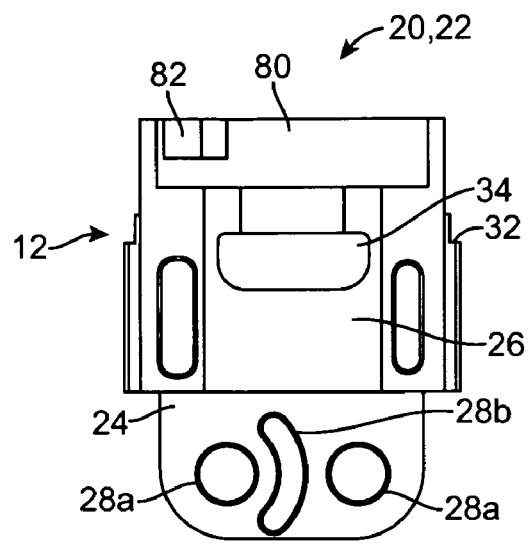
FIG. 8 illustrates a side view of half of a body of a spacer according to the present invention.

Turning now to FIG. 8, another variation of the body 12 will now be discussed wherein like reference numbers are used to describe like parts. The body 12 of the variation shown in FIG. 8 has the same clamshell construction with the left body piece 20 joined to a right body piece 22 to capture arms 14, 16 inside. With the right and left body pieces 20, 22 joined together, the body 12 is generally cylindrical. It has a cross-sectional size and shape that allows for implantation between adjacent spinous processes and facilitates delivery into a patient through a narrow port or cannula. The left and right body pieces 20, 22 are identical and therefore, FIG. 8 illustrates either the left or right body piece 20, 22.

Still referencing FIG. 8, the inside of the body 12 defines an arm receiving portion 24 and an actuator assembly receiving portion 26 with features formed in each of the left and right body pieces 20, 22 that together define the arm and actuator assembly receiving portions 24, 26. The arm receiving portion 24 includes slots or openings or apertures 28 that receive pins formed on the arms 14, 16 such that the pins rotate and/or translate inside the slots or apertures 28. In the variation shown in FIG. 8, in addition to two circular openings 28a, there is provided a curved slot 28b in each of the left and right body pieces 20, 22. The circular openings 28a and curved slot 28b are configured to receive pins 40 of arms 14, 16 that are illustrated in FIGS. 9a and 9b.

Figure 9A:
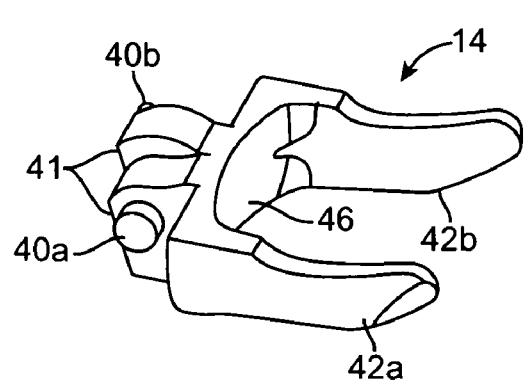
FIG. 9a illustrates a perspective view of a superior arm of a spacer according to the present invention.
Figure 9B:
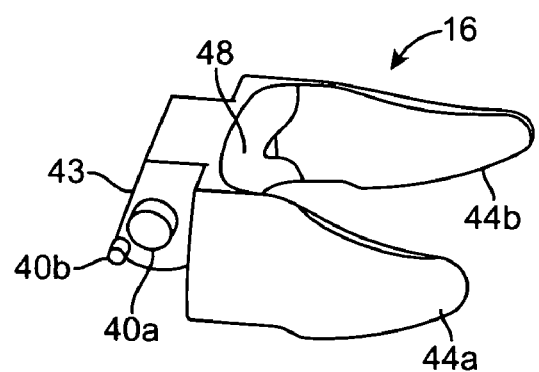
FIG. 9b illustrates a perspective view of an inferior arm of a spacer according to the present invention.

Turning now to FIGS. 9a and 9b, the superior arm 14 is shown in FIG. 9a, and the inferior arm 16 is shown in FIG. 9b. The superior and inferior arms 14, 16, include pins 40a and 40b for mating with the body 12, in particular, for mating with the openings 28a and slots 28b, respectively. Each side of the superior and inferior arms 14, 16 includes a circular first pin 40a configured for insertion into opening 28a such that the arms 14, 16 rotate with respect to the body 12. At least one side of each of the arms 14, 16 includes a second pin 40b configured for insertion into opening slot 28b. Slot 28b and pin 40b serve as a stop mechanism such that the rotation of the arms 14, 16 with respect to the body 12 is limited by pin 40b in slot 28b. While being deployed, the arms 14, 16 rotate to a position transverse to the longitudinal axis from a position parallel to the longitudinal axis wherein such rotation is arrested by pin 40b abutting the end of slot 28b. Other features of the arms 14, 16 shown in FIGS. 9a and 9b are substantially the same as described above and like reference numbers are used to describe the like parts.

Figure 10A:
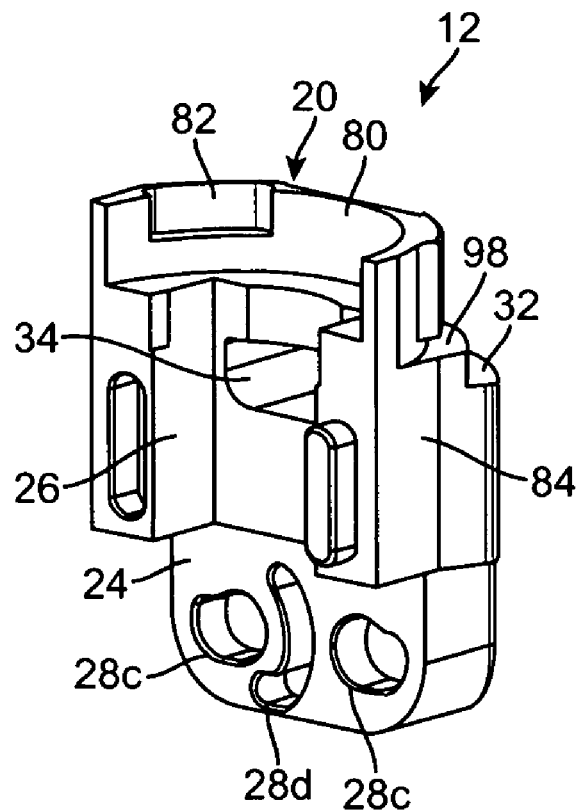
FIG. 10a illustrates a perspective view of half of a body of a spacer according to the present invention.
Figure 10B:
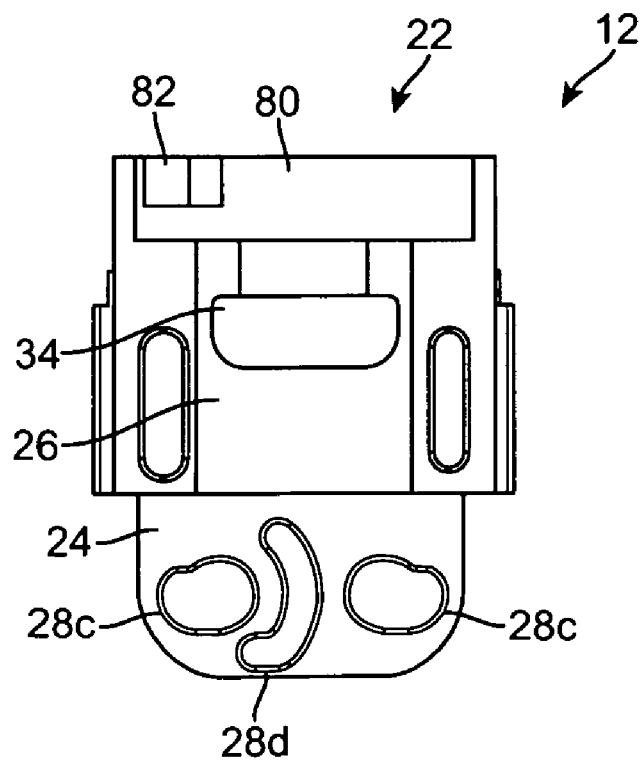
FIG. 10b illustrates a side view of half of a body of a spacer according to the present invention.

Turning now to FIGS. 10a and 10b, another variation of the spacer body 12 will now be discussed wherein like reference numbers are used to describe like parts. The body 12 of the spacer variation shown in FIGS. 10a and 10b has a clamshell construction as described above with the left body piece 20 joined to a right body piece 22 to capture arms 14, 16 inside. With the right and left body pieces 20, 22 joined together, the body 12 is generally cylindrical. It has a cross-sectional size and shape that allows for implantation between adjacent spinous processes and facilitates delivery into a patient through a narrow port or cannula. FIG. 10a shows the left body piece 20 and FIG. 10b shows the right body piece 22, however, the left and right body pieces 20, 22 are identical.

Still referencing FIGS. 10a and 10c, the inside of the body 12, formed by the conjunction of the left and right body pieces 20, 22, defines an arm receiving portion 24 and an actuator assembly receiving portion 26 with features formed in each of the left and right body pieces 20, 22 that together define the arm and actuator assembly receiving portions 24, 26. The arm receiving portion 24 includes slots or openings or apertures 28 that receive pins formed on the arms 14, 16 such that the pins rotate and/or translate inside the slots or apertures 28. In particular, in the variation shown in FIGS. 10a and 10b, two elongated openings 28c and a curved slot opening 28d are provided in each of the left and right body pieces 20, 22. The elongated openings 28c and curved opening 28d are configured to receive pins 40 of arms 14, 16 and serve as channels in which pins 40 can move. The curved slot 28d includes a straight distal portion for translating and extending the arms 14, 16 with respect to the body. Arms 14 and 16 with pins 40 configured to correspond to the left and right body pieces 20, 22 are shown in FIGS. 11a-11f.

Figure 11A:
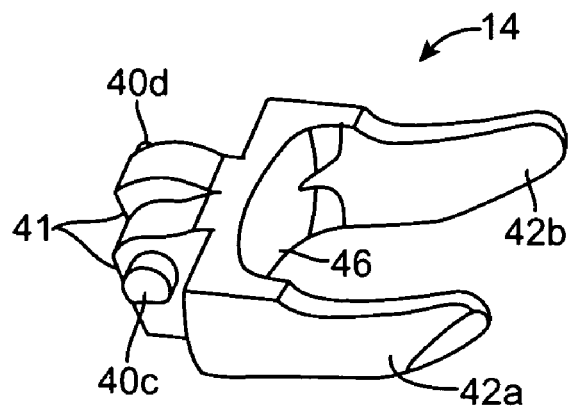
FIG. 11a illustrates a perspective view of a superior arm of a spacer according to the present invention.
Figure 11B:
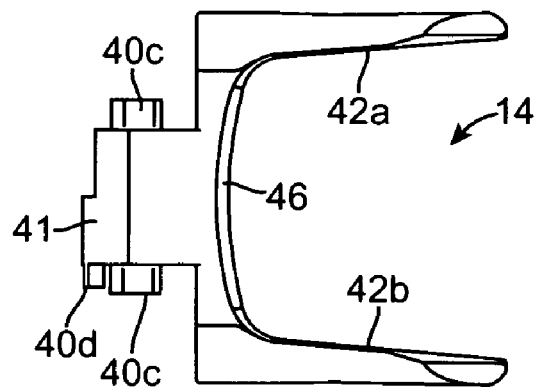
FIG. 11b illustrates a back view of a superior arm of a spacer according to the present invention.
Figure 11C:
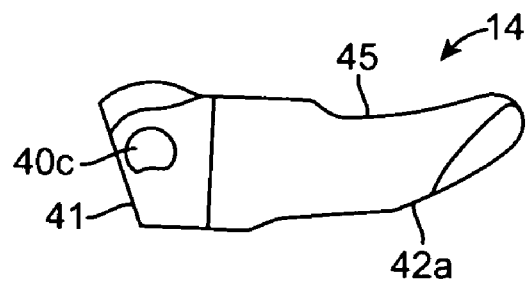
FIG. 11c illustrates a side view of a superior arm of a spacer according to the present invention.
Figure 11D:
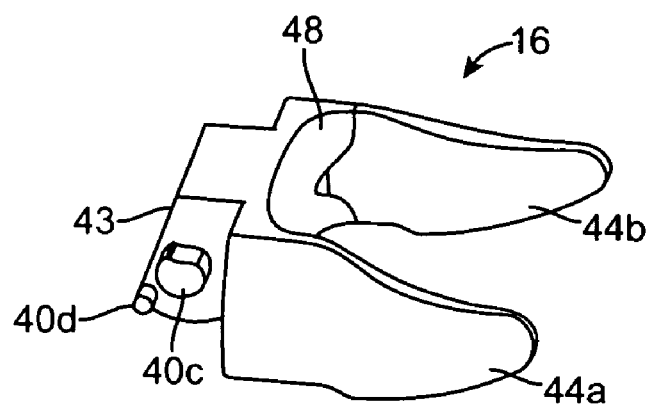
FIG. 11d illustrates a perspective view of an inferior arm of a spacer according to the present invention.
Figure 11E:
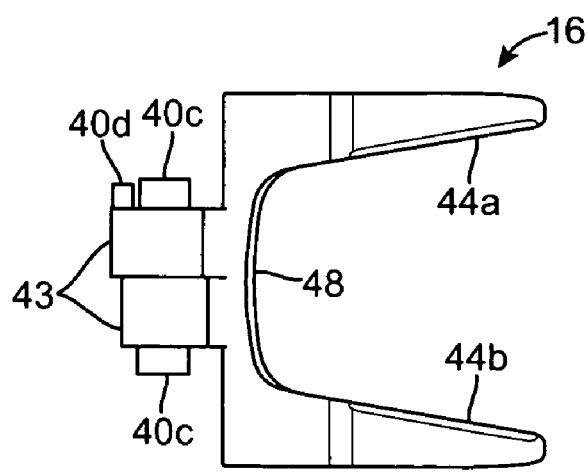
FIG. 11e illustrates a back view of an inferior arm of a spacer according to the present invention.
Figure 11F:
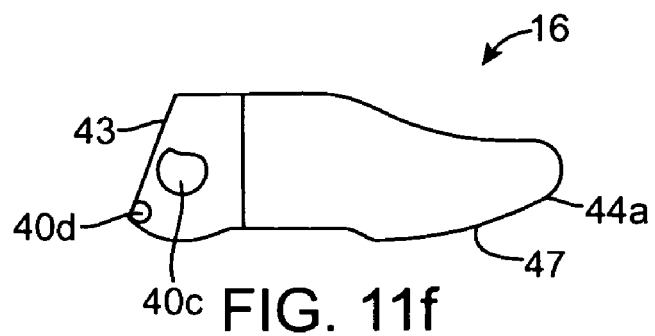
FIG. 11f illustrates a side view of an inferior arm of a spacer according to the present invention.

Turning now to FIGS. 11a-11f, the superior arm 14 is shown in FIGS. 11a-11c, and the inferior arm 16 is shown in FIGS. 11d-11f. The superior and inferior arms 14, 16, include pins 40c and 40d for mating with the body 12, in particular, for mating with the elongated openings 28c and curved slots 28d, respectively. Each side of the superior and inferior arms 14, 16 includes at least a first pin 40c configured for insertion into opening 28c such that the arms 14, 16 rotate with respect to the body 12 as well as translate with respect to the body 12. At least one side of each of the arms 14, 16 includes a second pin 40d configured for insertion into curved slot 28d such that the arms 14, 16 rotate with respect to the body 12 as well as translate with respect to the body 12. Slots 28d and openings 28c guide the movement of pins 40d and 40c, respectively therein as will be described with respect to FIGS. 12a-12d. Other features of the arms 14, 16 shown in FIGS. 11a-11f are substantially the same as described above and like reference numbers are used to describe the like parts.

Referring now to FIGS. 12a-12d, the spacer 10 is shown in a closed, undeployed configuration (FIG. 12a), a partially deployed or otherwise intermediary configuration (FIG. 12b), a deployed configuration (FIG. 12c), and a deployed and extended configuration (FIG. 12d). In moving from an undeployed to a deployed configuration, the semi-transparent views of the spacer 10 in FIGS. 12a-12d show the rotation and translation of the pins 40 of the arms 14, 16 in the slots 28 of the body 12. The translation of the pins 40 of the arms 14, 16 in the slots 28 of the body 12 is shown in moving from the first deployed configuration of FIG. 12c to the second deployed, extended configuration of FIG. 12d wherein the extension of the arms 14, 16 is in the direction of the arrows in FIG. 12d.

Such outward translation with respect to the body 12 is guided by the length and shape of the slots 28. Opening 28c is elongated and slot 28d includes a straight distal end configured to accommodate and guide the extension of arms 14, 16 away from the body 12. Reverse rotation of the spindle 86 moves the shaft 50 proximally with respect to the body 12 allowing the arms 14, 16 to close to any intermediary configuration between a deployed, extended configuration and an undeployed, closed configuration. This feature advantageously permits the surgeon to ease installation and positioning of the spacer with respect to patient anatomy as the arms 14, 16 can be deployed, undeployed and then re-deployed as often as necessary to position the spacer 10.

Figure 13A:
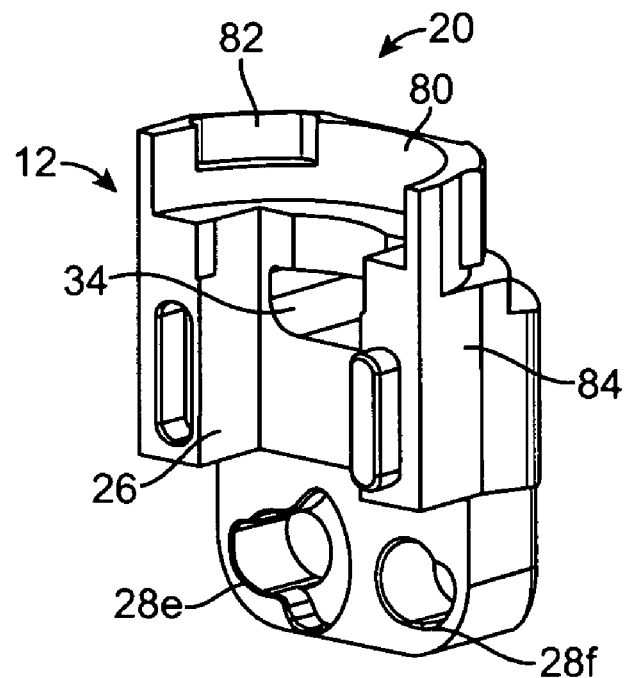
FIG. 13a illustrates a perspective view of half of a body of a spacer according to the present invention.
Figure 13B:
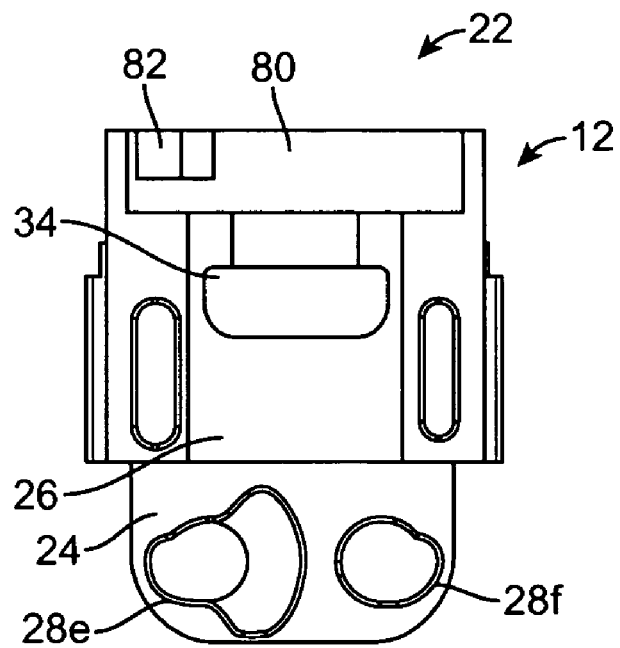
FIG. 13b illustrates a side view of half of a body of a spacer according to the present invention.

Turning now to FIGS. 13a and 13b, another variation of the spacer with yet another body 12 configuration will now be discussed wherein like reference numbers are used to describe like parts. The body 12 of the variation shown in FIGS. 13a and 13b has a clamshell construction as described above with a left body piece 20 joined to a right body piece 22 to capture arms 14, 16 inside. With the right and left body pieces 20, 22 joined together, the body 12 is generally cylindrical. It has a cross-sectional size and shape that allows for implantation between adjacent spinous processes and facilitates delivery into a patient through a narrow port or cannula. FIG. 13a shows the left body piece 20 and FIG. 13b shows the right body piece 22, however, the left and right body pieces 20, 22 are identical.

Still referencing FIGS. 13a and 13b, the inside of the body 12, formed by the conjunction of the left and right body pieces 20, 22, defines an arm receiving portion 24 and an actuator assembly receiving portion 26 that includes a spindle receiving portion 80 and lock receiving portion 82 with features formed in each of the left and right body pieces 20, 22 that together define the arm and actuator assembly receiving portions 24, 26. The arm receiving portion 24 includes slots or openings or apertures 28 that receive pins formed on the arms 14, 16 such that the pins rotate and/or translate inside the slots or apertures 28. In particular, in the variation shown in FIGS. 13a and 13b, a first opening 28e and a second opening 28f are provided in each of the left and right body pieces 20, 22. The first opening 28e includes a fanned recess. Both openings 28e and curved slot 28f are configured to receive pins 40 of arms 14, 16 and serve as channels that constrain the movement of the pins 40. In the variation shown, the openings 28e, 28f are configured to permit extension of the arms 14, 16 away from the body. Arms 14, 16 with pins 40 that are configured to correspond to the left and right body pieces 20, 22 are shown in FIGS. 14a-14f.

Figure 14A:
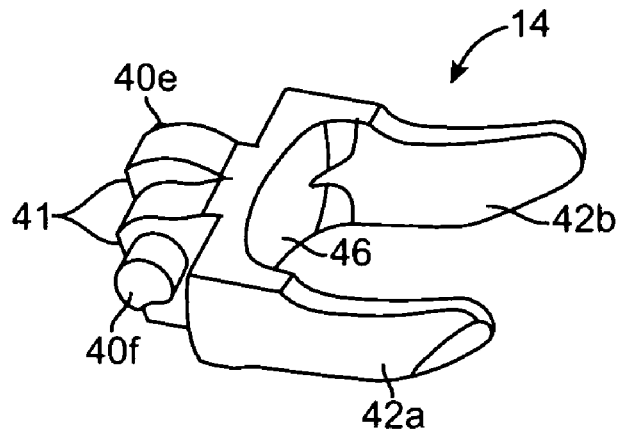
FIG. 14a illustrates a perspective view of a superior arm of a spacer according to the present invention.
Figure 14B:
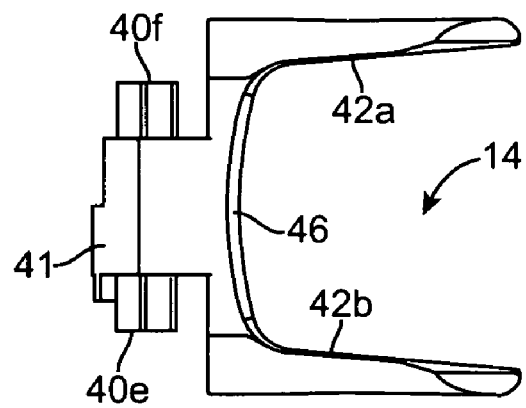
FIG. 14b illustrates a back view of a superior arm of a spacer according to the present invention.
Figure 14C:
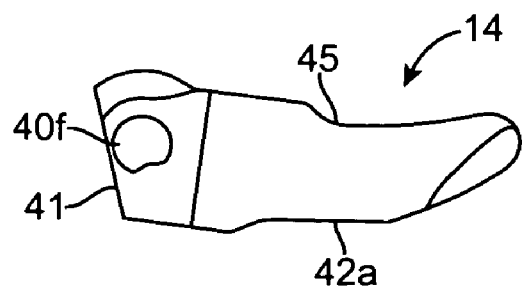
FIG. 14c illustrates a side view of a superior arm of a spacer according to the present invention.
Figure 14D:
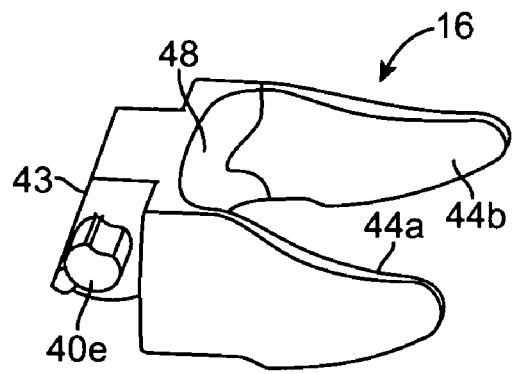
FIG. 14d illustrates a perspective view of an inferior arm of a spacer according to the present invention.
Figure 14E:
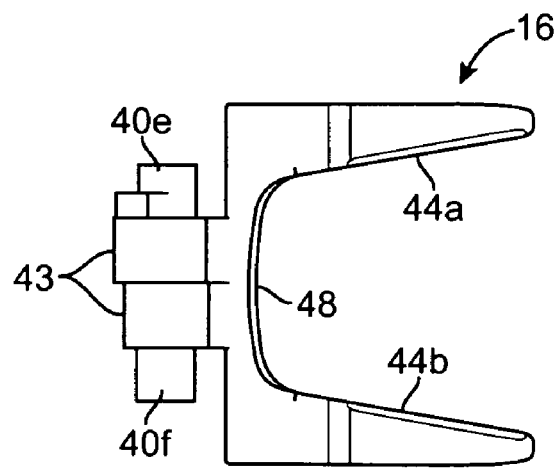
FIG. 14e illustrates a back view of an inferior arm of a spacer according to the present invention.
Figure 14F:
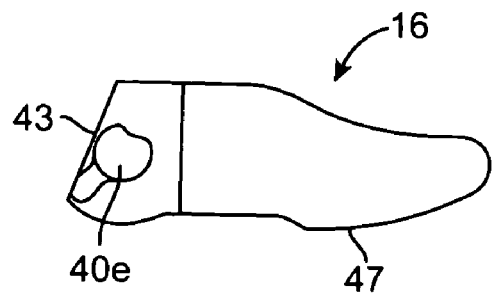
FIG. 14f illustrates a side view of an inferior arm of a spacer according to the present invention.

Turning now to FIGS. 14a-14f, the superior arm 14 is shown in FIGS. 14a-14c, and the inferior arm 16 is shown in FIGS. 14d-14f The superior and inferior arms 14, 16, include a first pin 40e and a second pin 40f for mating with the body 12, in particular, for mating with the first opening 28e and second opening 28f, respectively. At least one side of each of the superior and inferior arms 14, 16 includes a first pin 40e configured for insertion into opening 28e such that the arms 14, 16 rotate with respect to the body 12 as well as translate with respect to the body 12. At least the other side of each of the arms 14, 16 includes a second pin 40f configured for insertion into curved slot 28f such that the arms 14, 16 rotate with respect to the body 12 as well as translate with respect to the body 12. The first pin 40e includes a central portion integrally formed with a peripheral or projecting portion in what resembles a merging of two pins into one larger pin. This larger pin 40e advantageously provides a larger bearing surface capable of bearing larger loads in arresting rotation of the arms 14, 16. The first and second openings 28e, 28f guide the movement of pins 40e and 40f, respectively as will be described with respect to FIGS. 17a-17d. Other features of the arms 14, 16 shown in FIGS. 14a-14f are substantially the same as described above and like reference numbers are used to describe the like parts.

Figure 15A:
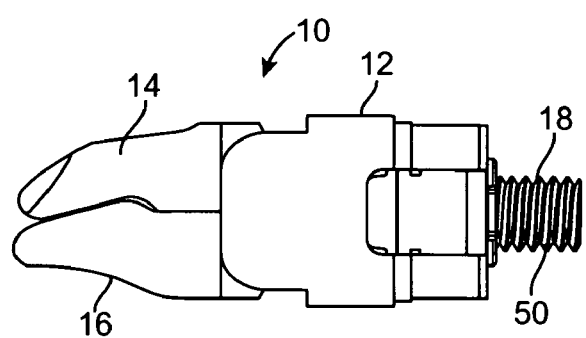
FIG. 15a illustrates a side view of a spacer in a closed, undeployed configuration according to the present invention.
Figure 15B:
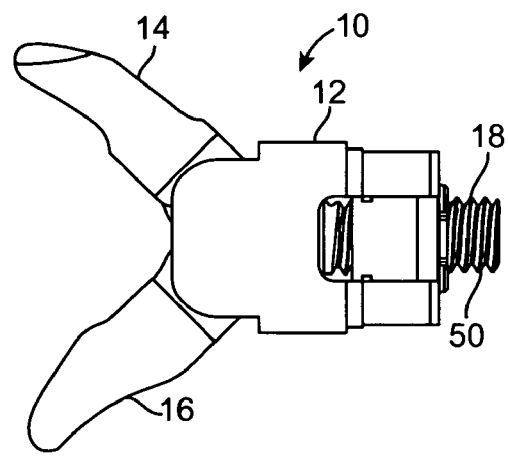
FIG. 15b illustrates a side view of a spacer in a partially deployed configuration according to the present invention.
Figure 15C:
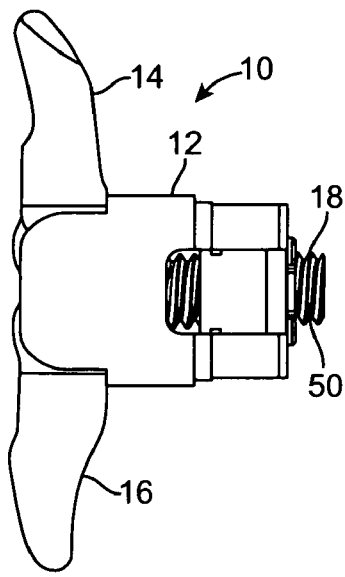
FIG. 15c illustrates a side view of a spacer in a deployed configuration according to the present invention.
Figure 15D:
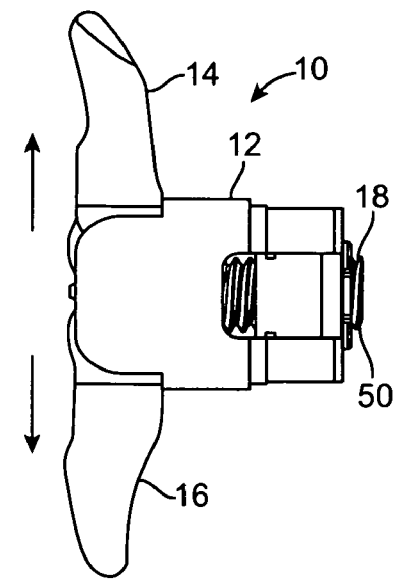
FIG. 15d illustrates a side view of a spacer in a deployed and extended configuration according to the present invention.

Referring now to FIGS. 15a-15d, the spacer 10 having a body 12 of FIGS. 13a and 13b is shown in a closed, undeployed configuration (FIG. 15a), a partially deployed or otherwise intermediary configuration (FIG. 15b), a deployed configuration (FIG. 15c), and a deployed and extended configuration (FIG. 15d).

Figure 16A:
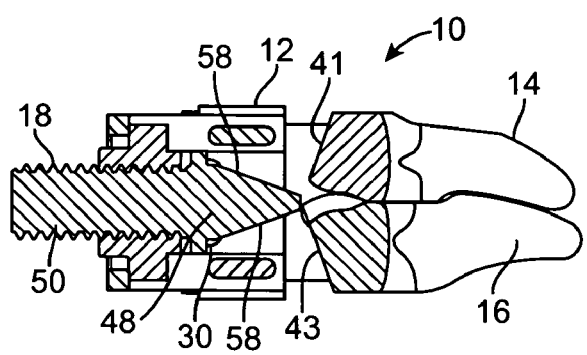
FIG. 16a illustrates a side, cross-sectional view of a spacer in a closed, undeployed configuration according to the present invention.
Figure 16B:
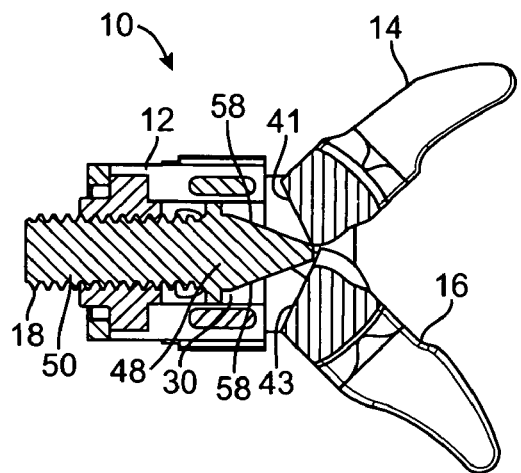
FIG. 16b illustrates a side, cross-sectional view of a spacer in a partially deployed configuration according to the present invention.
Figure 16C:
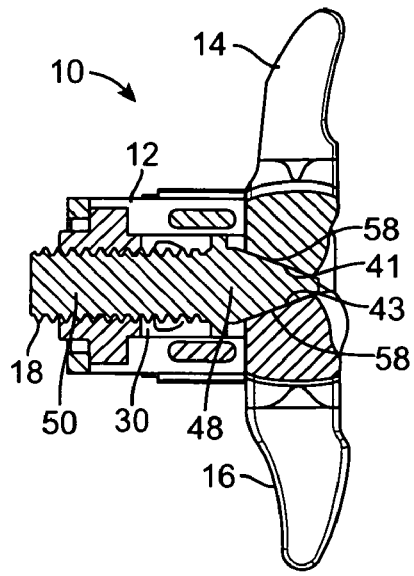
FIG. 16c illustrates a side, cross-sectional view of a spacer in a deployed configuration according to the present invention.
Figure 16D:
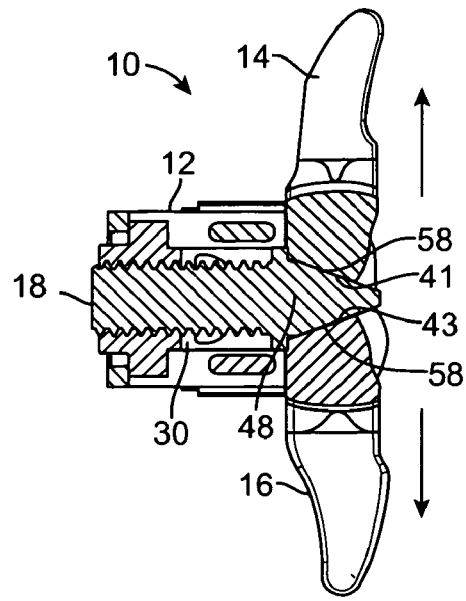
FIG. 16d illustrates a side, cross-sectional view of a spacer in a deployed and extended configuration according to the present invention.
Figure 17A:
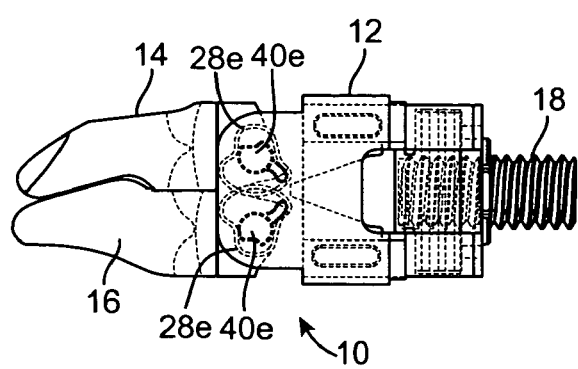
FIG. 17a illustrates a side, semi-transparent view of a spacer in a closed undeployed configuration according to the present invention.
Figure 17B:
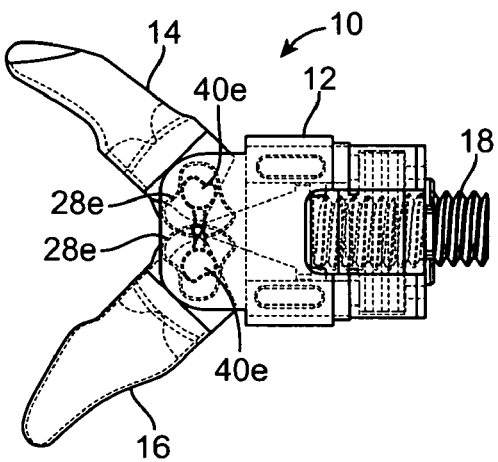
FIG. 17b illustrates a side, semi-transparent view of a spacer in a partially deployed configuration according to the present invention.
Figure 17C:
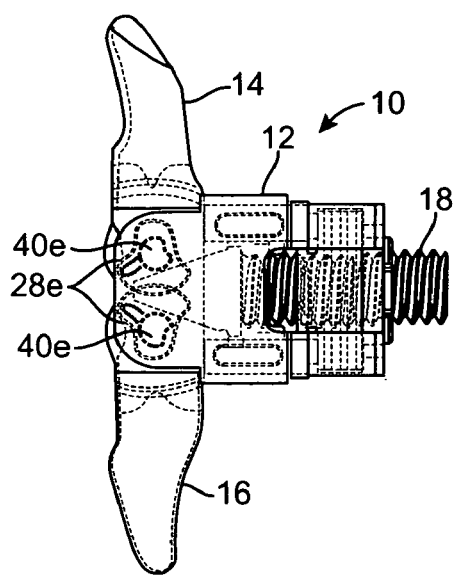
FIG. 17c illustrates a side, semi-transparent view of a spacer in a deployed configuration according to the present invention.
Figure 17D:
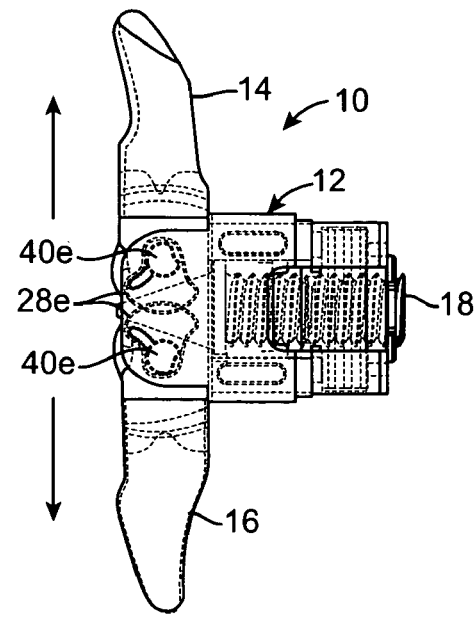
FIG. 17d illustrates a side, semi-transparent view of a spacer in a deployed and extended configuration according to the present invention.

Turning now to the cross-sectional views of the spacer 10 in FIGS. 16a-16d, as the spindle 86 is rotated and the shaft 50 advances within the passageway 30, the bearing surfaces 58 of the actuator 48 contact the superior and inferior caming surfaces 41, 43 of the superior and inferior arms 14, 16 turning the arms 14, 16 into rotation with respect to the body 12. Upon rotation, the bearing surfaces 58 of the actuator 48 slide with respect to the superior and inferior caming surfaces 41, 43 of the superior and inferior arms 14, 16. The arms 14, 16 rotate through an arc of approximately 90 degrees with respect to the body 12 into the deployed configuration (FIG. 16c) in which the superior and inferior extensions of the arms 14, 16 are substantially perpendicular to the longitudinal axis of the spacer 10 as shown in FIG. 16c and with further actuation, into a deployed and extended configuration (FIG. 16d) in which the superior and inferior extensions of the arms 14, 16 are substantially perpendicular to the longitudinal axis of the spacer 10 and the arms 14, 16 are moved away from the body 12 in a transverse direction to the longitudinal axis as shown by the arrows in FIG. 16d.

Turning now to FIGS. 17a-17d, semi-transparent views of the spacer 10 are shown. In moving from an undeployed to a deployed configuration, the rotation and translation of the pins 40e, 40f of the arms 14, 16 in the slots 28e, 28f of the body 12 is shown. Following rotation, the translation of the pins 40e, 40f of the arms 14, 16 in the slots 28e, 28f, respectively, is shown in moving from the first deployed configuration of FIG. 17c to the second deployed, extended configuration of FIG. 17d in the direction of the arrows in FIG. 17d. Such outward translation with respect to the body 12 is guided by the length and shape of the slots 28e, 28f. Reverse rotation of the spindle 86 moves the shaft 50 proximally with respect to the body 12 allowing the arms to close to any intermediary configuration between a deployed, extended configuration and an undeployed, closed configuration. This feature advantageously permits the surgeon to ease installation and positioning of the spacer with respect to patient anatomy.

To deliver and deploy the spacer 10 within the patient, the spacer 10 is releasably attached to an insertion instrument 80 at the proximal end of the spacer 10 via notches 34. The insertion instrument 80 includes a first assembly 102 connected to a second assembly 104 and a handle assembly 106.

Figure 18A:
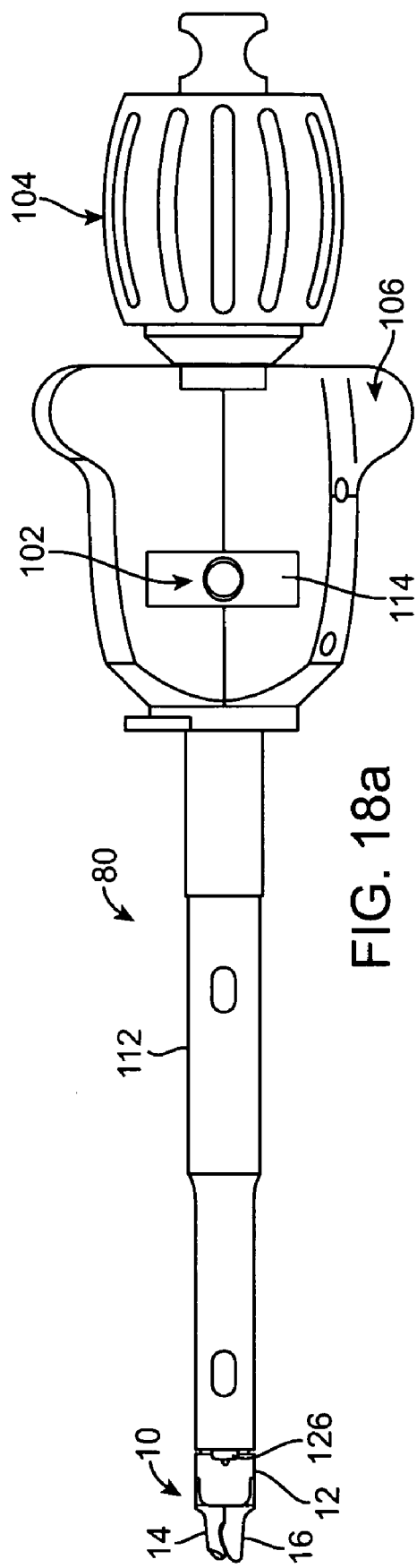
FIG. 18a illustrates a side view of an insertion instrument connected to a spacer in a closed, undeployed configuration according to the present invention.

The spacer 10 is provided or otherwise placed in its undeployed, closed state in juxtaposition to the insertion instrument 80 and connected thereto as shown in FIG. 18a. The longitudinal axis of the insertion instrument 80 is advantageously aligned with the longitudinal axis of the spacer 10 as shown. The delivery instrument 80 includes a first subassembly 102 to releasably clamp to the body 12 of the spacer 10 at a distal end of the insertion instrument 80. The first subassembly 102 includes an inner clamp shaft (not shown) having flexible prongs 126 at the distal end configured for attachment to the body 12 of the spacer 10 and, in particular, for insertion into the notches 34 of the spacer body 12. The first subassembly 102 includes an outer shaft 112 located over the inner clamp shaft and configured for relative motion with respect to one another via a control 114 located at the handle assembly 106. The control 114 is threaded to the outer shaft 112 such that rotation of the control 114 moves the outer shaft 112 along the longitudinal axis of the insertion instrument 80 over the inner clamp shaft to deflect and undeflect the prongs 126 to connect or disconnect the instrument 80 to or from the body 12. The first control 114 is activated at the handle of the insertion instrument 100 such that the first subassembly 102 is connected to the body 12 of the spacer 10. The first control 114 is rotated in one direction to advance the outer shaft 112 over the inner clamp shaft (not shown) deflecting the prongs 118 inwardly into the notches 34 on the body 12 of the spacer 10 to secure the spacer body 12 to the instrument as shown in FIG. 18a. Reverse rotation of the control 114 reverses the direction of translation of the outer shaft 112 to release the prongs 126 from the notches 34 and, thereby, release the spacer 10 from the instrument 80.

Still referencing FIG. 18a, the insertion instrument 80 includes a second subassembly 104 that is configured to connect to the actuator assembly 18 of the spacer 10. In particular, the second subassembly 104 includes means located at the distal end of the second subassembly 104 to activate the actuator assembly 18. In one variation, the second subassembly 104 is a pronged driver having an elongated shaft that is configured to be insertable into the notches 94 of the spindle 86 while the spacer 10 is connected to the instrument 80. As seen in FIG. 4b, there are two notches 94 oppositely located from each other in the spindle 86. The distal end of the driver includes prongs that correspond to the notches 94 and configured to be inserted into the notches 94. The second subassembly 104 is insertable at the proximal end of the instrument 80 and extends through the handle assembly 106 and through the inner shaft until the notches are engaged by the distal end. The removable driver 104 is rotatable with respect to the instrument 80 to rotate the spindle 86 and arrange the spacer 10 to and from deployed and undeployed configurations.

Figure 18B:
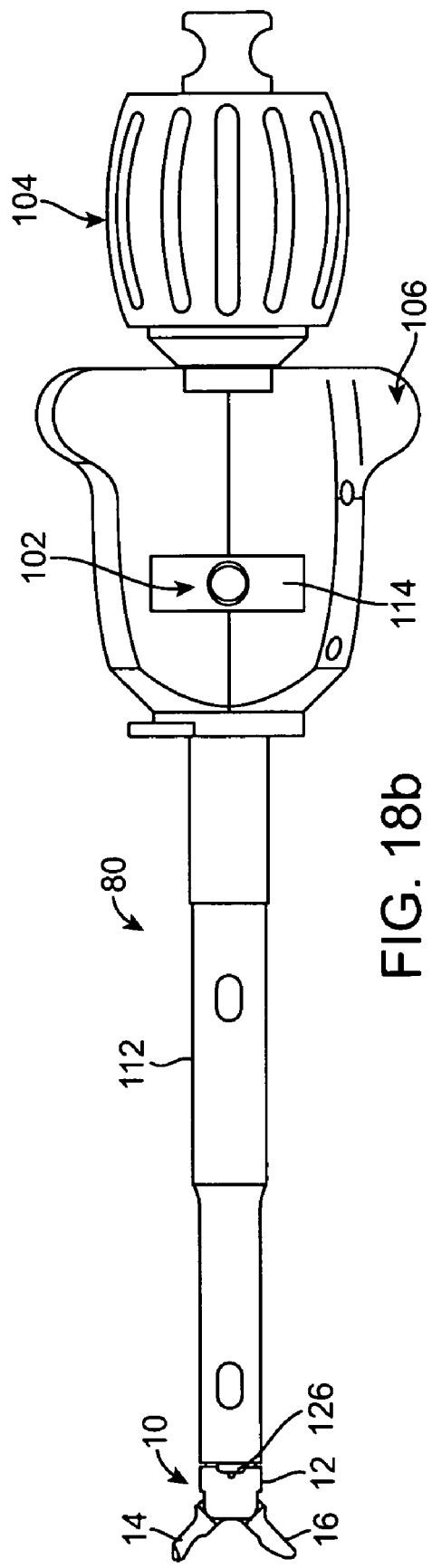
FIG. 18b illustrates a side view of an insertion instrument connected to a spacer in a partially deployed configuration according to the present invention.

To deliver and deploy the spacer 10 within the patient, the spacer 10 is releasably attached to a delivery instrument 80 at the proximal end of the spacer 10 as described. A small midline or lateral-to-midline incision is made in the patient for minimally-invasive percutaneous delivery. In one variation, the supraspinous ligament is avoided. In another variation, the supraspinous ligament is split longitudinally along the direction of the tissue fibers to create an opening for the instrument. Dilators may be further employed to create the opening. In the undeployed state with the arms 14, 16 in a closed orientation and attached to a delivery instrument 80, the spacer 10 is inserted into a port or cannula, if one is employed, which has been operatively positioned to an interspinous space within a patient's back and the spacer is passed through the cannula to the interspinous space between two adjacent vertebral bodies. The spacer 10 is advanced beyond the end of the cannula or, alternatively, the cannula is pulled proximately to uncover the spacer 10 connected to the instrument 80. Once in position, the second assembly 104 is inserted into the instrument 80 if not previously inserted to engage the spindle notches 94 and is rotated to rotate the spindle 86. The rotating spindle 86 then advances the actuator 48 and shaft 50 to begin deployment the spacer 10. Rotation in one direction, clockwise, for example, threadingly advances the shaft 50 through the spindle central bore 90 which then results in the actuator 48 contacting the superior and inferior caming surfaces 41, 43 of the superior and inferior arms 14, 16 to begin their deployment. FIG. 18b illustrates the superior arm 14 and the inferior arm 16 in a partially deployed position with the arms 14, 16 rotated away from the longitudinal axis. Rotation of the driver 104 turns the spindle 86 which in turn rotates the actuator shaft 50 threadingly advancing it with respect to the body 12 which distally advances the actuator 48 whose bearing surfaces 58 contact the superior and inferior camming surfaces 41, 43 pushing the superior and inferior arms 14, 16 into rotation about the pins 40 that are guided in the openings 28. The lock 88 snaps into the spindle teeth 102 advantageously locking the deployment of the arms at any degree of rotation of the spindle 86 to prevent the arms 14, 16 from folding and providing a tactile and audio feedback of the deployment progress. The lock 88 permits further rotation or de-rotation as desired.

The position of the arms 14, 16 in FIG. 18b may be considered to be one of many partially deployed configurations or intermediary configurations that are possible and from which the deployment of the arms 14, 16 is reversible with opposite rotation of the second assembly 104. With further advancement, the arms 14, 16 rotate through an arc of approximately 90 degrees into the deployed configuration in which the superior and inferior extensions are substantially perpendicular to the longitudinal axis of the spacer 10 as shown in FIG. 18c.

Figure 18C:
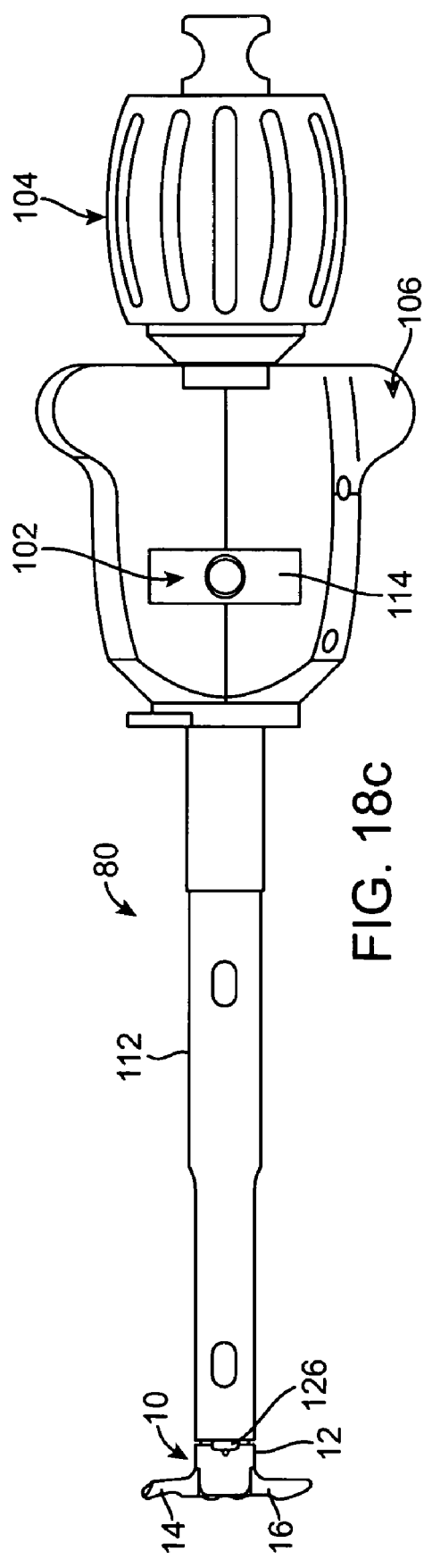
FIG. 18c illustrates a side view of an insertion instrument connected to a spacer in a deployed configuration according to the present invention.

Turning to FIG. 18c, there is shown an insertion instrument 80 connected to a spacer 10 in a first deployed configuration in which the arms 14, 16 are approximately 90 degrees perpendicular to the longitudinal axis or perpendicular to the initial undeployed configuration. Continued rotation of second assembly 104 rotates the spindle 86 and threads the shaft 50 further distally with respect to the body 12 of the spacer 10 pushing the bearing surfaces 58 further against the superior and inferior camming surfaces 41, 43. While in the first deployed configuration of FIG. 18c, the clinician can observe with fluoroscopy the positioning of the spacer 10 inside the patient and then choose to reposition the spacer 10 if desired. Repositioning of the spacer may involve undeploying the arms 14, 16 by rotating the spindle 86 via the second assembly 104 to rotate the arms into any one of the many undeployed configurations. The spacer may then be re-deployed into the desired location. This process can be repeated as necessary until the clinician has achieved the desired positioning of the spacer in the patient. Of course, inspection of the spacer 10 may be made via fluoroscopy while the spacer 10 is in an intermediate or partially deployed configuration such as that of FIG. 18b.

Figure 18D:
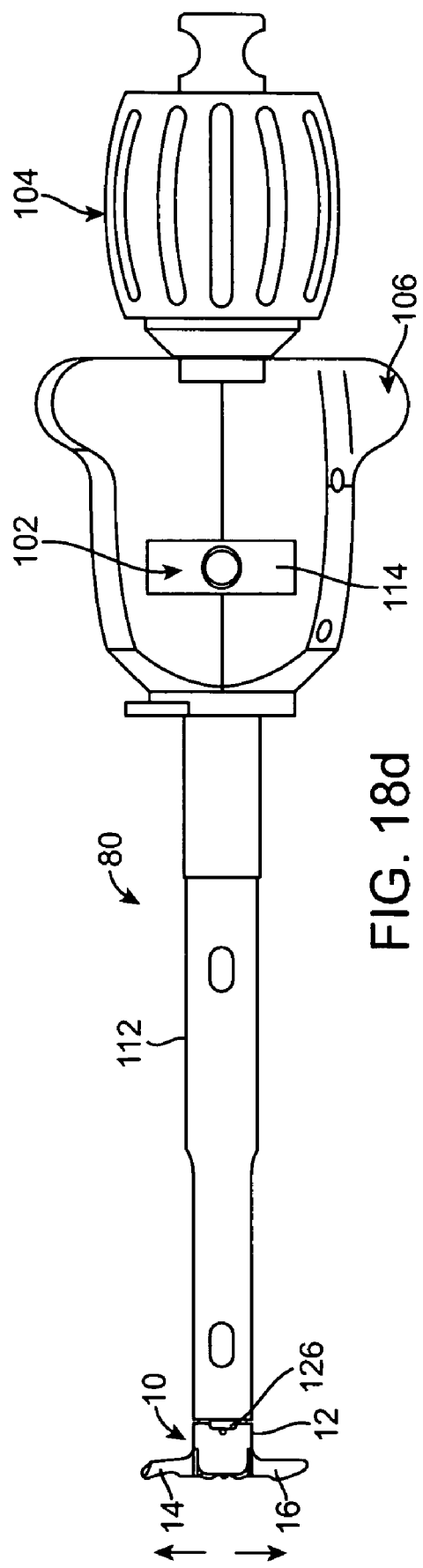
FIG. 18d illustrates a side view of an insertion instrument connected to a spacer in a deployed and extended configuration according to the present invention.

Even further advancement of the actuator shaft 50 via rotation of the second subassembly 104 from the first deployed configuration results in the spacer 10 assuming a second deployed configuration shown in FIG. 18d, if the spacer 10 is so configured as to allow a second deployed configuration. The second deployed configuration is an extended configuration as described above in which the superior and inferior arms 14, 16 extend transversely with respect to the longitudinal axis outwardly in the direction of the arrows in FIG. 18d. The spacer 10 is configured such that the outward translation of the arms 14, 16 follows the rotation into 90 degrees and is guided by the length and shape of the openings 28 in which the arms 14, 16 move. Once deployed, the superior arm 14 seats the superior spinous process and the inferior arm 16 seats the adjacent inferior spinous process. Such extension may also provide some distraction of the vertebral bodies.

Figure 19:
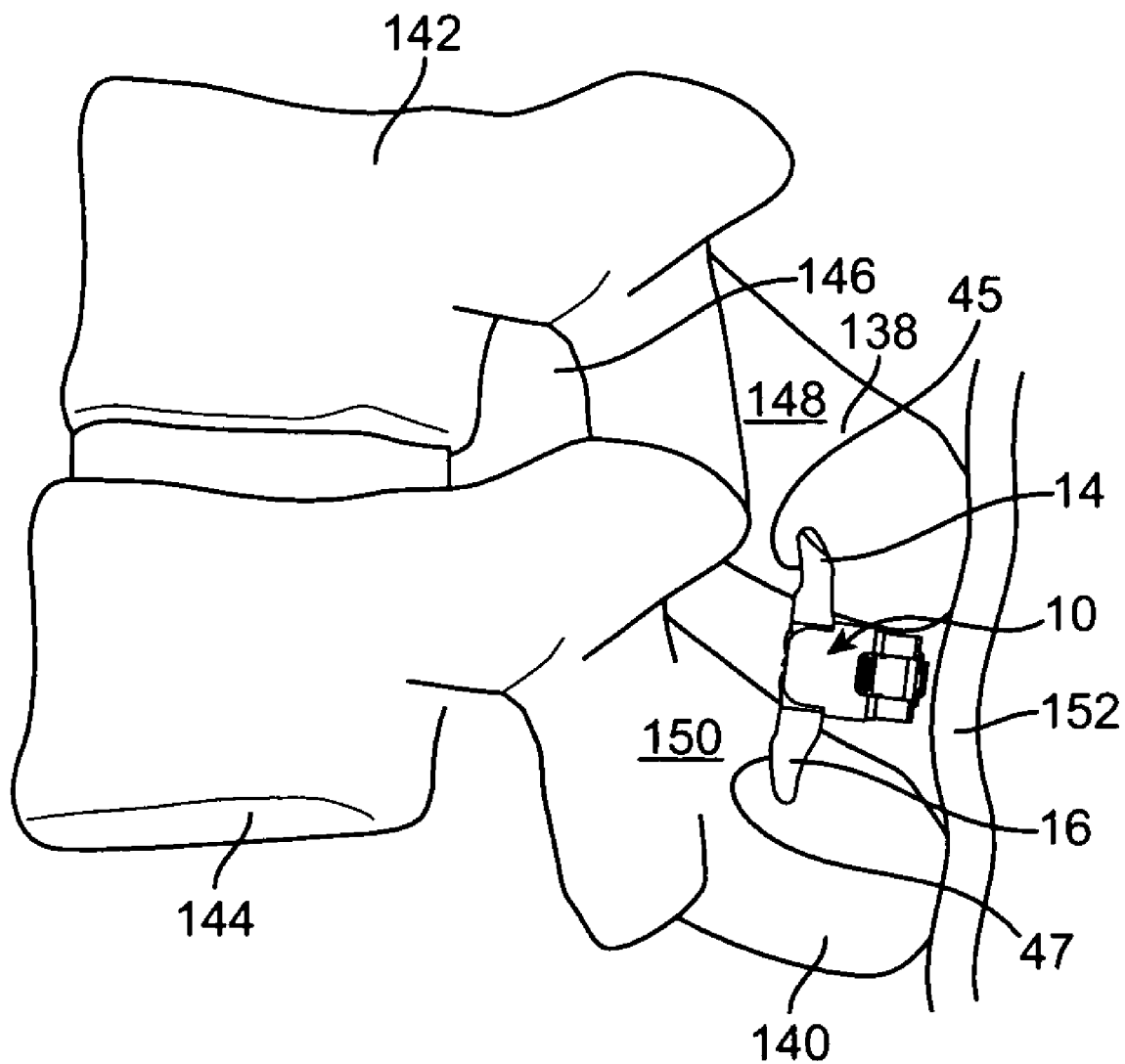
FIG. 19 illustrates a spacer according to the present invention deployed in an interspinous process space between two vertebral bodies and a supraspinous ligament.

Following deployment, the second assembly 104 may be removed. Control 114 is rotated in the opposite direction to release the body 12 from the instrument 80. The insertion instrument 80, thus released from the spacer 10, is removed from the patient leaving the spacer 10 implanted in the interspinous process space as shown in FIG. 19. In FIG. 19, the spacer 10 is shown with the superior arm 14 seating the superior spinous process 138 of a first vertebral body 142 and the inferior arm 16 seating the inferior spinous process 140 of an adjacent second vertebral body 144 providing sufficient distraction to open the neural foramen 146 to relieve pain. As mentioned above, the shape of the superior arm 14 is such that a superior concavity or curvature 45 is provided to conform to the widening of the superior spinous process 138 in an anterior direction toward the superior lamina 148 going in the anterior direction. In general, the superior arm 14 is shaped to conform to anatomy in the location in which it is seated. Likewise, as mentioned above, the shape of the inferior arm 16 is such that an inferior convexity or curvature 47 is provided to conform to the widening of the inferior spinous process 140 in an anterior direction toward the inferior lamina 150. The supraspinous ligament 152 is also shown in FIG. 19.

The spacer 10 is as easily and quickly removed from body of the patient as it is installed. The instrument 80 is inserted into an incision and reconnected to the spacer 10. The shaft 50 is rotated in the opposite direction via a driver 104 to fold the arms 14, 16 into a closed or undeployed configuration. In the undeployed configuration, the spacer 10 can be removed from the patient along with the instrument 80 or, of course, re-adjusted and re-positioned and then re-deployed as needed with the benefit of minimal invasiveness to the patient.

Any of the spacers disclosed herein are configured for implantation employing minimally invasive techniques including through a small percutaneous incision and through the superspinous ligament. Implantation through the superspinous ligament involves selective dissection of the superspinous ligament in which the fibers of the ligament are separated or spread apart from each other in a manner to maintain as much of the ligament intact as possible. This approach avoids crosswise dissection or cutting of the ligament and thereby reduces the healing time and minimizes the amount of instability to the affected spinal segment. While this approach is ideally suited to be performed through a posterior or midline incision, the approach may also be performed through one or more incisions made laterally of the spine with or without affect to the superspinous ligament. Of course, the spacer may also be implanted in a lateral approach that circumvents the superspinous ligament altogether as well as in open or mini-open procedures.

Other variations and features of the various mechanical spacers are covered by the present invention. For example, a spacer may include only a single arm which is configured to receive either the superior spinous process or the inferior spinous process. The surface of the spacer body opposite the side of the single arm may be contoured or otherwise configured to engage the opposing spinous process wherein the spacer is sized to be securely positioned in the interspinous space and provide the desired distraction of the spinous processes defining such space. The additional extension of the arm(s) subsequent to their initial deployment in order to seat or to effect the desired distraction between the vertebrae may be accomplished by expanding the body portion of the device instead of or in addition to extending the individual extension members 14, 16.

The extension arms of the subject device may be configured to be selectively movable subsequent to implantation, either to a fixed position prior to closure of the access site or otherwise enabled or allowed to move in response to normal spinal motion exerted on the device after deployment. The deployment angles of the extension arms may range from less than 90 degrees (relative to the longitudinal axis defined by the device body) or may extend beyond 90 degrees and remain stationary or be dynamic. Each extension member may be rotationally movable within a range that is different from that of the other extension members. Additionally, the individual superior and/or inferior extensions 42a, 42b, 44a, 44b may be movable in any direction relative to the strut or bridge extending between an arm pair or relative to the device body in order to provide shock absorption and/or function as a motion limiter, or serve as a lateral adjustment particularly during lateral bending and axial rotation of the spine. The manner of attachment or affixation of the extensions to the arms may be selected so as to provide movement of the extensions that is passive or active or both. In one variation, the saddle or distance between extensions 42a and 42b or between 44a and 44b can be made wider to assist in seating the spinous process and then narrowed to secure the spinous process positioned between extensions 42a and 42b or between 44a and 44b.

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

We claim:

1. An implantable spacer for placement between adjacent spinous processes comprising:
   a body defining a longitudinal axis;
   a first arm and a second arm both connected to the body and capable of movement with respect to the body; each arm defining a configuration for receiving a spinous process of a subject; each arm having a proximal caming surface;
   an actuator assembly connected to the body; the actuator assembly comprising:
      an actuator having at least one bearing surface;
      a shaft connected to the actuator and configured for movement with respect to the body; and
      a spindle;
   the actuator assembly is configured to move relative to the body such that rotation of the spindle moves the actuator such that the at least one bearing surface contacts at least one of the caming surfaces to move both of the arms from an undeployed configuration to a deployed configuration in which the arms receive adjacent spinous processes while the body is positioned between the spinous processes such that the longitudinal axis of the body extends in a posterior-anterior direction relative to a spine of the subject.

2. The spacer of claim 1 further including a retainer configured to retain the actuator and spindle with respect to the body such that the actuator moves and the spindle rotates relative to the body.

3. The spacer of claim 2 wherein the retainer includes at least one prong configured to attach to the body.

4. The spacer of claim 1 wherein the spindle includes an inner threaded surface and the shaft includes an outer threaded surface configured for threaded engagement with each other.

5. The spacer of claim 1 further including a lock configured to resist rotation of the spindle.

6. The spacer of claim 1 further including a lock having at least one tooth and the spindle further including a plurality of teeth on the other surface configured to engage the at least one tooth on the lock.

7. The spacer of claim 1 wherein each of the first and second arms includes at least one pin and the body includes corresponding apertures configured for connecting the first and second arms to the body at the pins such that the arms are movable with respect to the body.

8. The spacer of claim 7 wherein the apertures and pins are configured such that the first and second arms are capable of rotation with respect to the body.

9. The spacer of claim 7 wherein the apertures and pins are configured such that the first and second arms are capable of rotation and translation with respect to the body.

10. The spacer of claim 7 wherein the apertures and pins are configured such that the first and second arms are capable of rotation followed by translation with respect to the body.

11. The spacer of claim 1 wherein the first and second arms are configured for rotation with respect to the body.

12. The spacer of claim 1 wherein the first and second arms are configured for rotation and translation with respect to the body.

13. The spacer of claim 1 wherein the first and second arms are configured such that the first and second arms are capable of outwardly extending away from the body.

14. The spacer of claim 1 wherein the first and second arms rotate approximately 90 degrees into at least one deployed configuration in which the arms are approximately transverse to the longitudinal axis of the body; said rotation being from an undeployed configuration in which the arms are substantially parallel to the longitudinal axis of the body.

15. The spacer of claim 14 wherein at least one of the first and second arms extend outwardly with respect to the body in a direction substantially transverse to the longitudinal axis of the body.

16. The spacer of claim 1 wherein the first and second arms rotate approximately 90 degrees into at least one deployed configuration in which the arms are approximately transverse to the longitudinal axis of the body; said rotation being from an undeployed configuration in which the arms are substantially parallel to the longitudinal axis of the body; and wherein following said rotation upon further actuation the arms translate with respect to the body in a direction substantially transverse to longitudinal axis of the body.

17. The spacer of claim 1 wherein the body is configured for attachment to a spacer delivery instrument such that the longitudinal axis of the spacer delivery instrument is substantially aligned with the longitudinal axis of the spacer.

18. The spacer of claim 1 wherein the spindle includes notches for receiving a tool to rotate to the spindle with respect to the body.

19. The spacer of claim 1 wherein rotation of the spindle in one direction advances the actuator distally to engage the caming surfaces and deploy the arms into at least one deployed configuration and rotation of the spindle in an opposite direction moves the actuator proximally to permit the arms to fold into at least one undeployed or intermediary configuration.

20. The spacer of claim 1 wherein each arm has a pair of extensions and a saddle defining a configuration that is substantially U-shaped for seating a spinous process.

21. The spacer of claim 1 wherein the body defines a passageway and the actuator assembly is at least partially disposed inside the passageway.

22. The spacer of claim 1 wherein each arm has a substantially U-shaped portion, the substantially U-shaped portion of the first arm has a pair of elongate members with free ends configured to be positioned on either side of one of the spinous processes, and the substantially U-shaped portion of the second arm has a pair of elongate members with free ends configured to be positioned on either side of the other spinous process.

23. The spacer of claim 1 wherein each arm has a substantially U-shaped portion, and wherein the first arm and the second arm are configured to hold the body spaced apart from both of the spinous processes when the substantially U-shaped portion of the first arm receives and seats one of the spinous processes and the substantially U-shaped portion of the second arm receives and seats the adjacent spinous process.

24. The spacer of claim 1 wherein the actuator assembly is connected to the body such that the actuator is moveable relative to the body towards the proximal caming surfaces when the shaft is rotated relative to the body.

25. The spacer of claim 1 wherein the first arm and the second arm extend in a direction substantially parallel to the longitudinal axis of the body when both of the first arm and the second arm are in the undeployed configuration.

26. The spacer of claim 1, wherein the first arm and the second arm rotate away from the longitudinal axis of the body when both of the first arm and the second arm move from the undeployed configuration to the deployed configuration.

27. An implantable spacer for placement between adjacent spinous processes comprising:
   a body defining a longitudinal axis;
   a first arm and a second arm both connected to the body and capable of movement with respect to the body; each arm defining a configuration for receiving a spinous process; each arm having a proximal caming surface;
   an actuator assembly connected to the body; the actuator assembly comprising:
      an actuator having at least one bearing surface;
      a shaft connected to the actuator and configured for movement with respect to the body; and
      a spindle;
   a retainer configured to retain the actuator and the spindle with respect to the body such that the actuator moves and the spindle rotates relative to the body, wherein the retainer includes an opening configured to allow the shaft to pass through;
   wherein the actuator assembly is configured to move relative to the body such that rotation of the spindle moves the actuator such that the at least one bearing surface contacts at least one of the caming surfaces to move both of the arms from an undeployed configuration to a deployed configuration in which the arms receive adjacent spinous processes.

28. An implantable spacer for placement between adjacent spinous processes comprising:
   a body defining a longitudinal axis;
   a first arm and a second arm both connected to the body and capable of movement with respect to the body; each arm having a configuration for receiving a spinous process; each arm having a proximal caming surface;
   an actuator connected to the body and configured to move relative to the body to deploy the arms from an undeployed configuration wherein in the deployed configuration the arms seat adjacent spinous processes and the longitudinal axis of the body is positioned between the adjacent spinous processes and extends in a substantially posterior-anterior direction; and
   a lock configured to provide resistance to keep the arms in place.

29. The spacer of claim 28 wherein the lock is configured to provide resistance to the actuator while permitting the actuator relative movement with respect to the body.

30. The spacer of claim 28 further including a spindle threaded to the actuator; wherein the spindle includes an outer surface having a plurality of teeth and the lock includes at least one tooth configured to engage the plurality.

31. The spacer of claim 28 wherein the lock is configured to retain the actuator in place.

32. The spacer of claim 28 wherein the lock is releasable.

33. The spacer of claim 28 further including a spindle connected to the actuator and the lock being configured to provide resistance to the rotation of the spindle.

34. An implantable spacer for placement between adjacent spinous processes comprising:
   a body defining a longitudinal axis;
   a first arm and a second arm both connected to the body and capable of movement with respect to the body, each arm including a substantially U-shaped portion configured to receive and extend on either side of a spinous process;
   an actuator assembly connected to the body, the actuator assembly comprising:
      an actuator having at least one bearing surface;
      a shaft connected to the actuator and configured for movement with respect to the body; and
      a spindle;
   wherein the actuator assembly is configured to move relative to the body such that rotation of the spindle moves the actuator such that the at least one bearing surface contacts and moves both of the arms from an undeployed configuration to a deployed configuration in which the substantially U-shaped portions of the arms receive and extend on either side of the adjacent spinous processes.

35. The spacer of claim 34 wherein the substantially U-shaped portion of the first arm has a pair of elongate members with free ends configured to be positioned on either side of one of the spinous processes and the substantially U-shaped portion of the second arm has a pair of elongate members with free ends configured to be positioned on either side of the adjacent spinous process.

36. The spacer of claim 34 wherein the first arm and the second arm are configured to hold the body spaced apart from both of the spinous processes when the substantially U-shaped portion of the first arm receives and seats one of the spinous processes and the substantially U-shaped portion of the second arm receives and seats the adjacent spinous process.

* * * * *